United States Patent [19]

Smolanoff et al.

[11] Patent Number: 4,614,734

[45] Date of Patent: * Sep. 30, 1986

[54] PESTICIDAL PHOSPHOROAMIDO(DI)THIOATES

[75] Inventors: Joel R. Smolanoff, Chalfont, Pa.; J. Michael Fitzpatrick, Sao Paulo, Brazil; Janet Ollinger, Chalfont, Pa.

[73] Assignee: Rohm and Haas Company, Philadelphia, Pa.

[*] Notice: The portion of the term of this patent subsequent to Oct. 1, 2002 has been disclaimed.

[21] Appl. No.: 624,310

[22] Filed: Jun. 25, 1984

Related U.S. Application Data

[60] Division of Ser. No. 391,072, Jun. 22, 1982, Pat. No. 4,544,553, which is a continuation-in-part of Ser. No. 276,780, Jun. 24, 1982, abandoned.

[51] Int. Cl.$^4$ .................... A01N 57/08; A01N 57/02; C07F 9/24
[52] U.S. Cl. .................... 514/101; 514/113; 514/114; 514/128; 514/130; 514/137
[58] Field of Search ............... 260/940, 941, 945, 946, 260/947, 948, 949, 950, 951, 954, 956, 959; 548/117; 549/220; 514/101, 113, 114, 128, 130, 137

[56] References Cited

U.S. PATENT DOCUMENTS

| 3,399,213 | 8/1968 | Osborne | 260/326 |
|---|---|---|---|
| 3,511,635 | 5/1970 | Braxton, Jr. et al. | 71/87 |
| 3,657,426 | 4/1972 | Schroeder | 424/200 |
| 3,716,600 | 2/1973 | Magee | 260/959 |
| 3,760,043 | 9/1973 | Kishino et al. | 260/951 |
| 3,825,634 | 7/1979 | Magee | 260/956 |
| 3,845,172 | 10/1974 | Magee | 260/956 |
| 3,885,032 | 5/1975 | Magee | 424/212 |
| 3,914,417 | 10/1975 | Magee | 424/219 |
| 4,049,679 | 9/1977 | Magee | 260/503 |
| 4,110,443 | 8/1978 | Magee | 424/212 |
| 4,161,524 | 7/1979 | Kishino et al. | 424/215 |
| 4,263,288 | 4/1981 | Ollinger | 424/210 |
| 4,544,553 | 10/1985 | Smolanoff et al. | 514/92 |

OTHER PUBLICATIONS

*Soviet Inventors Illustrated* (Derwent Publication 1980), Week C05, Section C, p. 1, Abstract No. 08617C/05.
Derwent Abstract of Japans 70 12281 4/6/77.

Primary Examiner—Anton H. Sutto
Attorney, Agent, or Firm—John C. Demeter

[57] ABSTRACT

This invention relates to phosphoroamidothioate and phosphoroamidodithioate compounds, to compositions thereof which are useful as pesticides, for example, as athropodicides (that is, insecticides and acaricides), nematocides, and fungicides, and to a method of controlling pests, such as insects, acarids, nematodes, and fungi. The compounds of the invention are effective against soil insects, especially the corn rootworm, when applied by soil application techniques and are also effective when applied to agricultural plants and other plants by foliar application techniques.

38 Claims, No Drawings

PESTICIDAL PHOSPHOROAMIDO(DI)THIOATES

This application is a division of U.S. Ser. No. 391,072 filed June 22, 1982, now U.S. Pat. No. 4,544,553, which is a continuation-in-part application of U.S. Ser. No. 276,780 filed June 24, 1981, now abandoned.

BACKGROUND OF THE INVENTION

1. Field of the Invention

This invention relates to novel phosphoroamidothioate and phosphoroamidodithioate compounds, to compositions thereof which are useful as pesticides, for example, as arthropodicides (that is, insecticides and acaricides), nematocides, and fungicides, and to a method of controlling pests, such as insects, acarids, nematodes, and fungi. The compounds are effective when applied by soil application techniques and by foliar application techniques.

2. Description of the Prior Art

Ollinger, U.S. Pat. No. 4,263,288, issued Apr. 21, 1981, discloses acaricidal, insecticidal, and nematocidal phosphoroamidothioates having the formula

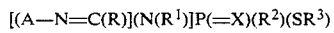

wherein
A is aryl,
R is hydrogen or alkyl,
$R^1$ is alkyl, cycloalkyl, alkenyl, alkynyl or aralkyl,
$R^2$ is alkylthio, aryloxy, or amino,
$R^3$ is alkyl, and
X is O or S.

The several Magee patents, U.S. Pat. Nos. 3,716,600, 4,049,679 (and continuation-in-part thereof, 4,110,443), 3,914,417, 3,845,172, 3,885,032, and 3,825,634, disclose insecticidal phosphoroamidothioates and phosphoroamidodithioates and methods of killing insects therewith. Column 18, lines 1-8 of U.S. Pat. No. 3,716,600 discloses broadly that, in addition to foliar application of the insecticidal compounds, one or more of the compounds may be applied in other liquid or solid formulations to the insects, their environment or hosts, for example, directly to plants or soil so as to effect control of insects coming into contact therewith. The compounds have the formula $(RY)(R^1S)P(=O)(N(R^3)(C(=O)R^2)$ wherein R, $R^1$, $R^2$, and $R^3$, respectively, broadly, are alkyl, alkenyl, alkynyl, and haloalkyl, and Y is O or S.

The abstract of Japanese Pat. No. 77012251 discloses N—acyl—O—alkyl—S—alkyl(alkoxy, alkylthio, alkenyl, phenyl, alkoxycarbonyl, cyano, carbamoyl)—phosphoroamidothioates having insecticidal activity and having the formula

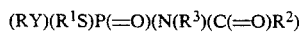

Osborne, U.S. Pat. No. 3,399,213, discloses parasiticidal and fungicidal acylphosphoroamidate compounds having the formulas

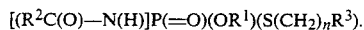

and

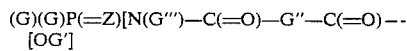

wherein G represents lower alkylamino, alkoxy, alkylthio, alkylphenyl, phenoxy, and substituted phenyl.

Braxton, Jr., et. al., U.S. Pat. No. 3,511,635, discloses herbicidal organophosphorous—nitrogen compounds having the formula

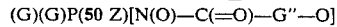

wherein
$R^1$ and $R^2$ are alkyl, alkenyl, diaryl, alkaryl, or aralkyl groups;
X and $X^1$ are O, S, or Se; and
n is an integer from 2-9.

Kishino et. al., U.S. Pat. No. 3,760,043, disclose O—phenyl—S—alkyl—N—alkyl—phosphoroamidothioates which possess fungicidal, acaricidal, insecticidal, and nematocidal properties and have the formula

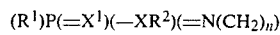

Schroeder, U.S. Pat. No. 3,657,426, discloses a method of controlling nematodes and other parasitic worm life existing in the soil at some stage of its life cycle by applying to the pests to be controlled or to the soil in which they live an effective amount of an O,O—dialkyl O-(1,2-dihydro-2-keto-1,6-dialkyl-4-pyridyl)phosphorothionate having the formula

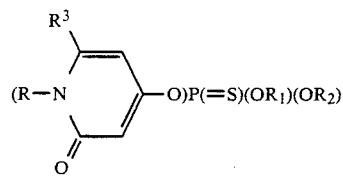

Although the prior art discloses phosphoroamidothioate and phosphoroamidodithioate compounds having pesticidal, including insecticidal, activity, there remains a need for pesticidal compounds having improved pesticidal efficacy, and diminished detrimental effects such as mammalian toxicity and environmental waste, especially against soil insects such as the corn rootworm.

The prior art, including the several Magee patents described above which constitute the closest art known, do not provide any specific teaching illustrative of the insecticidal activity of the compounds therein disclosed when applied in the soil to protect against soil organisms. It is well known to those skilled in the art that organophosphates having a high order of contact insecticidal efficacy when applied to aerial, or foliar, portions of plants offer relatively little economic value as plant protectants when applied, or introduced, into the soil environment of the plants. Organophosphates tend to be susceptible to rapid degradative processes in the soil due to the combination of such factors as the hydrolytic action of soil moisture, unfavorable soil pH conditions, both of the above being exacerbated by the presence of soil microflora and fauna capable of rendering the insecticidal compound inactive. Application of a pesticide to the soil in ordinary agricultural practice does not necessarily or usually coincide with the presence of susceptible life stages of the target pest. For example, the hatching of insect eggs may be either delayed or it may occur over an interval of several days to several or many weeks. Insect ova are not generally affected by organophosphate pesticides. Thus, pesticidal compounds having satisfactory residual activity, especially in the soil—pesticidal compounds that retain their pesticidal efficacy under atmosphere conditions over an interval of several days to several or many weeks—are required in order to assure satisfactory protection of plants against soil insects. Further, it is highly desirable that such pesticidal compounds having activity persistent over an interval of several days to several or many weeks elicit control over a diverse selection of soil organisms that are agricultural pests.

SUMMARY OF THE INVENTION

It is an object of the invention to provide compounds, and compositions thereof, which are effective as pesticides, for example, as arthropodicides (including insecticides and acaricides), as nematocides, and as fungicides when applied by soil application or by foliar application techniques, especially against soil insects, for example the corn rootworm, and to provide a method for controlling said pests.

These and other objects as will become apparent, achieved by the present invention which comprises

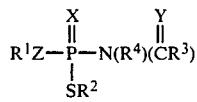
(I)

wherein:
$R^1$ is unsubstituted or substituted $(C_1-C_4)$alkyl wherein the substituent can be from one to four of the same or different bromo, chloro or fluoro groups;
$(C_3-C_6)$alkenyl;
$(C_3-C_6)$alkynyl;
unsubstituted or substituted phenyl wherein the substituent can be from one to three of the same or different alkyl, haloalkyl containing one to three of the same or different halo, halo, alkoxy, alkylthio, cyano, nitro, amino, or mono— or di—alkylamino, wherein the alkyl moiety is straight or branched chain and contains from one to three carbon atoms; or
unsubstituted or substituted phenyl($C_1-C_3$)alkyl wherein the substituent is on the phenyl ring and wherein the substituent can be from one to three of the same or different alkyl, haloalkyl containing one to three of the same or different halo, halo, alkoxy, alkylthio, cyano, nitro, amino, or mono— and di—alkylamino groups, wherein the alkyl moiety is straight or branched chain and contains from one to three carbon atoms;
$R^2$ is unsubstituted or substituted $(C_2-C_5)$alkyl wherein the substituent can be from one to three of the same or different alkyl, halo, alkoxy, alkylthio, cyano, nitro, amino, or mono— or di—alkylamino, wherein the alkyl moiety is straight or branched chain and contains from one to three carbon atoms or, when X and Y are both S, $CH_3$; or
$(C_3-C_6)$alkenyl;
$(C_3-C_6)$alkynyl;
$(C_3-C_6)$cycloaliphatic or heterocycloaliphatic;
unsubstituted or substituted phenyl wherein the substituent can be from one to three of the same or different alkyl, haloalkyl containing one to three of the same or different halo, halo, alkoxy, alkylthio, cyano, nitro, amino, or mono— or di—alkylamino, wherein the alkyl moiety is straight or branched chain and contains from one to three carbon atoms;
or
unsubstituted or substituted phenyl($C_1-C_3$)alkyl wherein the substituent is on the phenyl ring and wherein the substituent can be from one to three of the same or different alkyl, haloalkyl containing one to three of the same or different halo, halo, alkoxy, alkylthio, cyano, nitro, amino, or mono— and di—alkylamino groups, wherein the alkyl moiety is straight or branched chain and contains from one to three carbon atoms;
$R^3$ is hydrogen;
methyl;
trifluoromethyl;
carbo($C_1-C_4$)alkoxy; or
thiocarbo($C_1-C_4$)alkoxy;
$R^4$ is hydrogen;
unsubstituted or substituted $(C_1-C_7)$alkyl wherein the substituent can be one to three of the same or different carbo($C_1-C_4$)alkoxy, halo, alkoxy, benzoyl, alkylthio, cyano, nitro, unsubstituted or substituted phenoxy or phenylthio wherein the substituent can be from one to three of the same or different alkyl, alkoxy, halo, cyano, nitro, or alkylthio, or amino or mono— or di—alkylamino, wherein the alkyl moiety is straight or branched chain and contains from one to three carbon atoms; unsubstituted or substituted $(C_3-C_4)$alkenyl wherein the substituent can be from one to three of the same or different phenyl, alkyl, carbo($C_1-C_4$)alkoxy, bromo, chloro or fluoro groups;
$(C_3-C_6)$alkynyl;
unsubstituted or substituted phenyl wherein the substituent can be from one to five of the same or different halo or from one to three of the same or different alkyl, haloalkyl containing one to three of the same or different halo, alkoxy, alkylthio, cyano, nitro, amino, or mono— or di—alkylamino, wherein the alkyl moiety is straight or branched chain and contains from one to three carbon atoms;
or
unsubstituted or substituted phenyl, or naphthyl, ($C_1-C_3$)alkyl wherein the substituent is on the phenyl ring and wherein the substituent can be from one to five of the same or different halo or from one to three of the same or different alkyl, haloalkyl containing one to three of the same or different halo, alkoxy, alkylthio, benzyloxy, methylenedioxy, cyano, nitro, amino, or mono— or di—alkylamino groups, wherein the alkyl moiety is straight or branched chain and contains from one to three carbon atoms;
X, Y and Z are independently O or S provided that both X and Y are not O at the same time except that, in the case that X and Y are both O and Z is S, then $R^1$ is n—$C_3H_7$ or s—$C_4H_9$, $R^2$ is s—$C_4H_9$, $R^3$ is H, and $\bar{R}^4$ is $CH_3$.

In another aspect, this invention comprises a pesticidal composition, especially an insecticidal composition comprising a pesticidally effective amount of the compound of the invention defined herein above.

In yet another aspect, this invention comprises a method of controlling pests, insects, nematodes, acarids, and fungi, especially soil insects and pests, which comprises applying to the pests, insects, nematodes, acarids and fungi comprising applying on or in the soil or to the loci of plants to be freed from infestation a pesticidally or insecticidally effective amount of an active compound having the formula (I) defined herein above, or of a compound of formula (I) above except that X, Y and Z are independently O or S wherein X and Y may both be O at the same time.

In the practice of the method of the invention, the active compound may be applied to the soil, absorbed by plants grown in the soil, and ultimately ingested by the pests, insects, nematodes, acarids or fungi by means of ingestion of the plant part(s). This means of application is referred to as "systemic" application. Alternatively, the active compound may be applied to the soil and contacted therein with the insects and other pests to be controlled. This means of application is referred to as "soil" application. In another alternative the active compound may be foliarly applied to the plants to be freed from insects and other pests.

When using the compounds defined above, the method of the invention is especially effective against soil insects when the active compound is applied on or in the soil in order to effect direct contact with the insects or other pests, including nematodes, acarids and fungi. By "pests" is meant organisms including arthropods, which in turn includes insects and acarids, nematodes, and fungi, which organisms attack agricultural plants.

In a preferred embodiment for soil application, this invention comprises a compound according to formula (I) wherein:

$R^1$ is unsubstituted or substituted ($C_1$-$C_4$)alkyl wherein the substituent can be from one to three of the same or different bromo, chloro or fluoro groups;

unsubstituted or substituted phenyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms; or unsubstituted or substituted phenyl($C_1$-$C_3$)alkyl wherein the substituent is on the phenyl ring and wherein the substituent can be from one to three of the same or different alkyl, haloalkyl, halo, alkoxy, alkylthio, cyano, nitro, amino, or mono— and di—alkylamino groups, wherein the alkyl moiety is straight or branched chain and contains from one to three carbon atoms;

$R^2$ is unsubstituted or substituted ($C_2$-$C_5$)alkyl wherein the substituent can be from one to three of the same or different alkyl, halo, alkoxy, alkylthio, cyano, nitro, amino, or mono— or di—alkylamino, wherein the alkyl moiety is straight or branched chain and contains from one to three carbon atoms;
($C_3$-$C_6$)alkenyl;
($C_3$-$C_6$)cycloaliphatic or heterocycloaliphatic;
unsubstituted or substituted phenyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms; or unsubstituted or substituted phenyl($C_1$-$C_3$)alkyl wherein the substituent is on the phenyl ring and wherein the substituent can be from one to three of the same or different alkyl, haloalkyl, halo, alkoxy, alkylthio, cyano, nitro, amino, or mono— and di—alkylamino groups, wherein the alkyl moiety is straight or branched chain and contains from one to three carbon atoms;

$R^3$ is hydrogen;
methyl; or
trifluoromethyl; and $R^4$ is hydrogen;
unsubstituted or substituted ($C_1$-$C_7$)alkyl wherein the substituent can be one to three of the same or different carbo($C_1$-$C_4$)alkoxy, halo, alkoxy, alkylthio, cyano, nitro, unsubstituted or substituted phenoxy or phenylthio wherein the substituent can be from one to three of the same or different alkyl, alkoxy, halo, cyano, nitro, or alkylthio, or amino or mono— or di—alkylamino, wherein the alkyl moiety is straight or branched chain and contains from one to three carbon atoms;
($C_3$-$C_6$)alkenyl;
($C_3$-$C_6$)alkynyl;
unsubstituted or substituted phenyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms; or unsubstituted or substituted phenyl($C_1$-$C_3$)alkyl wherein the substituent is on the phenyl lring and wherein the substituent can be from one to three of the same or different alkyl, haloalkyl, halo, alkoxy, alkylthio, cyano, nitro, amino, or mono— and di—alkylamino groups, wherein the alkyl moiety is straight or branched chain and contains from one to three carbon atoms.

In a more preferred embodiment for soil application, this invention comprises a compound according to formula (I) wherein:

$R^1$ is methyl, ethyl, 2,2,2-trifluoroethyl, phenyl or benzyl;

$R^2$ is unsubstituted straight or branched chain ($C_3$-$C_5$)alkyl, phenyl or benzyl;

$R^3$ is hydrogen, methyl, or trifluoromethyl; and $R^4$ is methyl, ethyl, n—propyl, propenyl or unsubstituted or substituted benzyl wherein the substituent is on the phenyl ring and wherein the substituent can be from one to three of the same or different ($C_1$-$C_3$)alkyl, fluoro, chloro, bromo, methoxy, trifluoromethyl, nitro, or cyano groups.

In a most preferred embodiment for soil application, this invention comprises a compound according to formula (I) wherein:

$R^1$ is methyl, ethyl, or 2,2,2-trifluoroethyl;
$R^2$ is n—propyl, 3-pentyl, or 1-methylpropyl;
$R^3$ is hydrogen;
$R^4$ is methyl, ethyl, or substituted benzyl wherein the substituent is on the phenyl ring and wherein the substituent can be from one to two of the same or different ($C_1$-$C_3$)alkyl, fluoro, chloro, bromo, methoxy, trifluoromethyl, nitro, or cyano groups;
X and Y are, independently, O or S; and
Z is O.

Especially preferred embodiments of this invention comprise compounds having the following formulas:
($H_5C_2O$)P(S)(S sec—$C_4H_9$)(N($C_2H_5$)(CHO));
($H_5C_2O$)P(S)(S sec—$C_4H_9$)(N($C_2H_5$)(CHS));
($H_5C_2O$)P(S)(S sec—$C_4H_9$)(N($CH_3$)(CHO));
($H_5C_2O$)P(O)(S sec—$C_4H_9$)(N($C_2H_5$)(CHS)); and

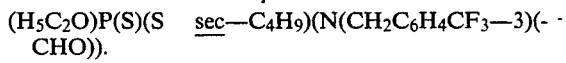(H$_5$C$_2$O)P(S)(S sec—C$_4$H$_9$)(N(CH$_2$C$_6$H$_4$CF$_3$—3)(-CHO)).

The development of the class of compounds described above led to the preparation of analogous compounds which were found to possess advantageous pesticidal efficacy when applied to agricultural plants by foliar application techniques. In a preferred embodiment for foliar application, the invention comprises a compound having the formula

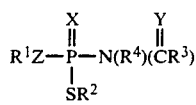

wherein:

R$^1$ is unsubstituted or substituted (C$_1$–C$_4$)alkyl wherein the substituent can be one (C$_1$–C$_4$)alkoxy or from one to three of the same or different bromo, chloro or fluoro groups;
(C$_3$–C$_6$)alkenyl;
(C$_3$–C$_6$)alkynyl;
unsubstituted or substituted phenyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms; or
unsubstituted or substituted phenyl(C$_1$–C$_3$)alkyl wherein the substituent is on the phenyl ring and wherein the substituent can be from one to three of the same or different alkyl, haloalkyl, halo, alkoxy, alkylthio, cyano, nitro, amino, or mono— and di—alkylamino groups, wherein the alkyl moiety is straight or branched chain and contains from one to three carbon atoms;

R$^2$ is unsubstituted or substituted C$_2$–C$_5$)alkyl wherein the substituent can be from one to three of the same of different alkyl, halo, alkoxy, alkylthio, cyano, nitro, amino, or mono— or di—alkylamino, wherein the alkyl moiety is straight or branched chain and contains from one to three carbon atoms; or
(C$_3$–C$_6$)alkenyl;
(C$_3$–C$_6$)alkynyl;
(C$_3$–C$_6$)cycloaliphatic or heterocycloaliphatic;
unsubstituted or substituted phenyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms; or
unsubstituted or substituted phenyl(C$_1$–C$_3$)alkyl wherein the substituent is on the phenyl ring and wherein the substituent can be from one to three of the same or different alkyl, haloalkyl, halo, alkoxy, alkylthio, cyano, nitro, amino, or mono— or di—alkylamino groups, wherein the alkyl moiety is straight or branched chain and contains from one to three carbon atoms;

R$^3$ is hydrogen;

R$^4$ is substituted (C$_1$–C$_7$)alkyl wherein the substituent can be one to three of the same or different phenylcarbonyl, carbo(C$_1$–C$_4$)alkoxy, halo, alkoxy, benzoyl, alkylthio, cyano, nitro, unsubstituted or substituted phenoxy or phenylthio wherein the substituent can be from one to three of the same or different alkyl, alkoxy, halo, cyano, nitro, or alkylthio, or amino or mono— or di—alkylamino, wherein the alkyl moiety is straight or branched chain and contains from one to three carbon atoms;
unsubstituted or substituted (C$_3$–C$_6$)alkenyl wherein the substituent can be from one to three of the same or different phenyl, carbo(C$_1$–C$_4$)alkoxy, bromo, chloro or fluoro groups;
(C$_3$–C$_6$)alkynyl;
unsubstituted or substituted phenyl, or naphthyl, (C$_1$–C$_3$)alkyl wherein the substituent is on the phenyl ring and wherein the substituent can be from one to five of the same or different halo or from one to three of the same or different alkyl, haloalkyl containing one to three of the same or different halo, alkoxy, alkylthio, cyano, nitro, amino, or mono— and di—alkyamino groups, wherein the alkyl moiety is straight or branched chain and contains from one to three carbon atoms; and X, Y and Z are each O.

In a more preferred embodiment for foliar application, this invention comprises a compound according to formula (I) wherein R$^1$ is unsubstituted or substituted (C$_1$–C$_4$)alkyl wherein the substituent can be from one to three of the same or different bromo, chloro or fluoro groups;
unsubstituted or substituted phenyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms; or
unsubstituted or substituted phenyl(C$_1$–C$_3$)alkyl wherein the substituent is on the phenyl ring and wherein the substituent can be from one to three of the same or different alkyl, haloalkyl, halo, alkoxy, alkylthio, cyano, nitro, amino, or mono— or di—alkylamino groups, wherein the alkyl moiety is straight or branched chain and contains from one to three carbon atoms;

R$^2$ is unsubstituted or substituted (C$_2$–C$_5$)alkyl wherein the substituent can be from one to three of the same or different alkyl, haloalkyl, halo, alkoxy, alkylthio, cyano, nitro, amino, or mono— or di—alkylamino, wherein the alkyl moiety is straight or branched chain and contains from one to three carbon atoms;
(C$_3$–C$_6$)alkenyl;
(C$_3$–C$_6$)cycloaliphatic or heterocycloaliphatic;
unsubstituted or substituted phenyl wherein the substituent can be from one to three of the same or different alkyl, haloalkyl, halo, alkoxy, alkythio, cyano, nitro, amino, or mono— or di—alkylamino, wherein the alkyl moiety is straight or branched chain and contains from one to three carbon atoms; or unsubstituted or substituted phenyl(C$_1$–C$_3$)alkyl wherein the substituent is on the phenyl ring and wherein the substituent can be from one to three of the same or different alkyl, haloalkyl, halo, alkoxy, alkylthio, cyano, nitro, amino, or mono— or di—alkylamino groups; wherein the alkyl moiety is straight or branched chain and contains from one to three carbon atoms;

R$^3$ is hydrogen;

R⁴ is substituted (C$_1$–C$_7$)alkyl wherein the substituent can be one to three of the same or different carbo(C$_1$–C$_4$)alkoxy, halo, alkoxy, alkylthio, cyano, nitro, unsubstituted or substituted phenoxy or phenylthio wherein the substituent can be from one to three of the same or different alkyl, alkoxy, halo, cyano, nitro, alkylthio, amino, or mono— or di—alkylamino, wherein the alkyl moiety is straight or branched chain and contains from one to three carbon atoms;

(C$_3$–C$_6$)alkenyl;

(C$_3$–C$_6$)alkynyl;

unsubstituted or substituted phenyl(C$_1$–C$_3$)alkyl wherein the substitutent is on the phenyl ring and wherein the substituent can be from one to five of the same or different halo or from one to three of the same or different haloalkyl containing one to three of the same or different halo, alkoxy, alkylthio, cyano, nitro, amino, or mono— or di—alkylamino groups, wherein the alkyl moiety is straight or branched chain and contains from one to three carbon atoms;

In a most preferred embodiment for foliar application, this invention comprises a compound according to formula (I) wherein R$^1$ is methyl, ethyl, 2,2,2-trifluoromethyl, phenyl, or benzyl;

R$^2$ is unsubstituted straight or branched chain (C$_3$–C$_5$)alkyl, phenyl, or benzyl;

R$^3$ is hydrogen; and

R$^4$ is unsubstituted or substituted benzyl wherein the substituent is on the phenyl ring and wherein the substituent can be from one to two of the same or different (C$_1$–C$_3$)alkyl, fluoro, chloro, bromo, trifluoromethyl, nitro or cyano groups.

In an especially preferred embodiment for foliar application, this invention comprises a compound according to formula (I) wherein:

R$^1$ is methyl, ethyl, or 2,2,2-trifluoroethyl;

R$^2$ is n—propyl, 3-pentyl, or 1-methylpropyl;

R$^3$ hydrogen; and

R$^4$ is unsubstituted or substituted benzyl wherein the substituent can be from one to two (C$_1$–C$_3$)alkyl, fluoro, chloro, bromo, trifluoromethyl, nitro or cyano groups.

Compounds illustrative of the invention include the following:

N-methyl-N-hydrogenthiocarbonyl-O-ethyl-S-n-butyl phosphoroamidothioate

N-methyl N-hydrogenthiocarbonyl O-ethyl S-n-butyl phosphoroamidodithioate

N-methyl N-hydrogencarbonyl O-ethyl S-n-butyl phosphoroamidodithioate

N-methyl N-hydrogenthiocarbonyl O-ethyl S-(2-methylpropyl)phosphoroamidothioate

N-methyl N-hydrogenthiocarbonyl O-ethyl S-(2-methylpropyl)phosphoroamidodithioate N-methyl N-hydrogencarbonyl O-ethyl S-(2-methylpropyl)phosphoroamidodithioate N-methyl N-hydrogenthiocarbonyl O-ethyl S-(1-pentyl)phosphoroamidothioate N-methyl N-hydrogenthiocarbonyl O-ethyl S-(1-pentyl)phosphoroamidodithioate N-methyl N-hydrogencarbonyl O-ethyl S-(1-pentyl)-phosphoroamidodithioate N-methyl N-hydrogencarbonyl O-ethyl S-(2-methylbutyl)phosphoroamidodithioate N-methyl N-hydrogenthiocarbonyl O-ethyl S-(2-methylbutyl)phosphoroamidothioate N-methyl N-hydrogenthiocarbonyl O-ethyl S-(2-methylbutyl)phosphoroamidodithioate N-methyl N-hydrogenthiocarbonyl O-ethyl S-(1-methylbutyl)phosphoroamidothioate N-methyl N-hydrogenthiocarbonyl O-ethyl S-(1-methylbutyl)phosphoroamidodithioate N-methyl N-hydrogencarbonyl O-ethyl S-(1-methylbutyl)phosphoroamidodithioate N-methyl N-hydrogenthiocarbonyl O-ethyl S-(3-methylbutyl)phosphoroamidothioate N-methyl N-hydrogenthiocarbonyl O-ethyl S-(3-methylbutyl)phosphoroamidodithioate N-methyl N-hydrogencarbonyl O-ethyl S-(3-methylbutyl)phosphoroamidodithioate N-methyl N-hydrogenthiocarbonyl O-ethyl S-(2,2-dimethylpropyl)phosphoroamidothioate N-methyl N-hydrogenthiocarbonyl O-ethyl S-(2,2-dimethylpropyl)phosphoroamidodithioate N-methyl N-hydrogencarbonyl O-ethyl S-(2,2-dimethylpropyl)phosphoroamidodithioate N-methyl N-hydrogenthiocarbonyl O-ethyl S-(2-methoxyethyl)phosphoroamidothioate N-methyl N-hydrogenthiocarbonyl O-ethyl S-(2-methoxyethyl)phosphoroamidodithioate N-methyl N-hydrogencarbonyl O-ethyl S-(2-methoxyethyl)phosphoroamidodithioate N-methyl N-hydrogencarbonyl O-ethyl S-(3-nitropropyl)phosphoroamidodithioate N-methyl N-hydrogenthiocarbonyl O-ethyl S-(3-nitro propyl)phosphoroamidodithioate N-methyl N-hydrogenthiocarbonyl O-ethyl S-(2-cyanoethyl)phosphoroamidothioate N-methyl N-hydrogenthiocarbonyl O-ethyl S-(2-cyanoethyl)phosphoroamidodithioate N-methyl N-hydrogencarbonyl O-ethyl S-(2-cyanoethyl)phosphoroamidodithioate N-methyl N-hydrogencarbonyl O-ethyl S-(3-chloropropyl)phosphoroamidodithioate N-methyl N-hydrogenthiocarbonyl O-ethyl S-(3-chloropropyl)phosphoroamidothioate N-methyl N-hydrogenthiocarbonyl O-ethyl S-(3-chloropropyl)phosphoroamidodithioate N-methyl N-hydrogencarbonyl O-ethyl S-(2-fluoroethyl)phosphoroamidodithioate N-methyl N-hydrogenthiocarbonyl O-ethyl S-(2-fluoroethyl)phosphoroamidothioate N-methyl N-hydrogenthiocarbonyl O-ethyl S-(2-fluoroethyl)phosophoroamidodithioate N-methyl N-hydrogenthiocarbonyl O-ethyl S-ethylthiomethyl phosphoroamidothioate N-methyl N-hydrogenthiocarbonyl O-ethyl S-ethylthioethyl phosphoroamidodithioate N-methyl N-hydrogencarbonyl O-ethyl S-ethylthiomethyl phosphoroamidodithioate N-methyl N-hydrogencarbonyl O-ethyl S-[(1,1-dimethylethyl)thiomethyl]phosphoroamidodithioate N-methyl N-hydrogenthiocarbonyl O-ethyl S-[(1,1-dimethylethyl)thiomethyl]phosphoroamidothioate N-methyl N-hydrogenthiocarbonyl O-ethyl S-[(1,1-dimethylethyl)thiomethyl]phosphoroamidodithioate N-methyl N-hydrogencarbonyl O-ethyl S-(2-bromoallyl)phosphoroamidodithioate N-methyl N-hydrogenthiocarbonyl O-ethyl S-(2-bromoallyl)phosphoroamidodithioate N-methyl N-hydrogenthiocarbonyl O-ethyl S-(2-bromoallyl)phosphoroamidothioate
N-methyl N-hydrogencarbonyl O-ethyl S-(3-butenyl)phosphoroamidodithioate
N-methyl N-hydrogenthiocarbonyl O-ethyl S-(3-butenyl)phosphoroamidothioate
N-methyl N-hydrogenthiocarbonyl O-ethyl S-(3-butenyl)phosphoroamidodithioate
N-methyl N-hydrogenthiocarbonyl O-ethyl S-(2-butenyl)phosphoroamidothioate
N-methyl N-hydrogenthiocarbonyl O-ethyl S-(2-butenyl)phosphoroamidodithioate
N-methyl N-hydrogencarbonyl O-ethyl S-(2-butenyl)phosphoroamidodithioate
N-methyl N-hydrogencarbonyl O-ethyl S-(5-hexenyl)phosphoroamidodithioate
N-methyl N-hydrogenthiocarbonyl O-ethyl S-(5-hexenyl)phosphoroamidothioate
N-methyl N-hydrogenthiocarbonyl O-ethyl S-(5-hexenyl)phosphoroamidodithioate
N-methyl N-hydrogenthiocarbonyl O-ethyl S-propargyl phosphoroamidothioate
N-methyl N-hydrogenthiocarbonyl O-ethyl S-propargyl phosphoroamidodithioate
N-methyl N-hydrogencarbonyl O-ethyl S-propargyl phosphoroamidodithioate
N-methyl N-hydrogenthiocarbonyl O-ethyl S-phenyl phosphoroamidothioate
N-methyl N-hydrogenthiocarbonyl O-ethyl S-phenyl phosphoroamidodithioate
N-methyl N-hydrogencarbonyl O-ethyl S-phenyl phosphoroamidodithioate
N-methyl N-hydrogencarbonyl O-ethyl S-trichlorophenyl phosphoroamidodithioate
N-methyl N-hydrogenthiocarbonyl O-ethyl S-trichlorophenyl phosphoroamidothioate
N-methyl N-hydrogenthiocarbonyl O-ethyl S-trichlorophenyl phosphoroamidodithioate
N-methyl N-hydrogenthiocarbonyl O-ethyl S-(1-phenylethyl)phosphoroamidothioate
N-methyl N-hydrogenthiocarbonyl O-ethyl S-(1-phenylethyl)phosphoroamidodithioate
N-methyl N-hydrogencarbonyl O-ethyl S-(1-phenylethyl)phosphoroamidodithioate
N-methyl N-hydrogencarbonyl O-ethyl S-(5-phenyl-1-pentyl)phosphoroamidodithioate
N-methyl N-hydrogenthiocarbonyl O-ethyl S-(5-phenyl-1-pentyl)phosphoroamidodithioate
N-methyl N-methylcarbonyl O-ethyl S-(1-methylpropyl)phosphoroamidodithioate
N-methyl N-butylcarbonyl O-ethyl S-(1-methylpropyl)phosphoroamidodithioate
N-heptyl N-hydrogencarbonyl O-ethyl S-(1-methylpropyl)phosphoroamidodithioate
N-heptyl N-hydrogenthiocarbonyl O-ethyl S-(1-methylpropyl)phosphoroamidothioate
N-heptyl N-hydrogenthiocarbonyl O-ethyl S-(1-methylpropyl)phosphoroamidodithioate
N-(3-methoxypropyl)N-hydrogenthiocarbonyl O-ethyl S-(1-methylpropyl)phosphoroamidothioate
N-(3-methoxypropyl)N-hydrogenthiocarbonyl O-ethyl S-(1-methylpropyl)phosphoroamidodithioate
N-(3-methoxylpropyl)N-hydrogencarbonyl O-ethyl S-(1-methylpropyl)phosphoroamidodithioate
N-(3-chloropropyl)N-hydrogencarbonyl O-ethyl S-(1-methylpropyl)phosphoroamidodithioate
N-(3-chloropropyl)N-hydrogenthiocarbonyl O-ethyl S-(1-methylpropyl)phosphoroamidothioate
N-(3-chloropropyl)N-hydrogenthiocarbonyl O-ethyl S-(1-methylpropyl)phosphoroamidodithioate
N-(2-fluoroethyl)N-hydrogenthiocarbonyl O-ethyl S-(1-methylpropyl)phosphoroamidothioate
N-(2-fluoroethyl)N-hydrogencarbonyl O-ethyl S-(1-methylpropyl)phosphoroamidodithioate
N-(2-butenyl)N-hydrogencarbonyl O-ethyl S-(1-methylpropyl)phosphoroamidodithioate
N-(2-butenyl)N-hydrogenthiocarbonyl O-ethyl S-(1-methylpropyl)phosphoroamidothioate
N-(2-butenyl)N-hydrogenthiocarbonyl O-ethyl S-(1-methylpropyl)phosphoroamidodithioate
N-(5-hexenyl)N-hydrogencarbonyl O-ethyl S-(1-methylpropyl)phosphoroamidodithioate
N-(5-hexenyl)N-hydrogenthiocarbonyl O-ethyl S-(1-methylpropyl)phosphoroamidodithioate
N-(5-hexenyl)N-hydrogenthiocarbonyl O-ethyl S-(1-methylpropyl)phosphoroamidothiaote
N-[(2-carboethoxy)-1-propenyl]N-hydrogenthiocarbonyl O-ethyl S-(1 methylpropyl) phosphoroamidothioate
N-[(2-carboethoxy)-1-propenyl]N-hydrogenthiocarbonyl O-ethyl S-(1-methylpropyl)phosphoroamidodithioate
N-[(2-carboethoxy)-1-propenyl]N-hydrogencarbonyl O-ethyl S-(1-methylpropyl)phosphoroamidodithioate
N-(3-hexyn-1-yl)N-hydrogencarbonyl O-ethyl S-(1-methylpropyl)phosphoroamidodithioate
N-(3-hexyn-1-yl)N-hydrogenthiocarbonyl O-ethyl S-(1-methylpropyl)phosphoroamidodithioate
N-(3-hexyn-1-yl)N-hydrogenthiocarbonyl O-ethyl S-(1-methylpropyl)phosphoroamidothioate
N-phenyl N-hydrogencarbonyl O-ethyl S-(1-methylpropyl)phosphoroamidodithioate
N-phenyl N-hydrogenthiocarbonyl O-ethyl S-(1-methylpropyl)phosphoroamidothioate
N-phenyl N-hydrogenthiocarbonyl O-ethyl S-(1-methylpropyl)phosphoroamidodithioate
N-p-chlorobenzyl N-hydrogenthiocarbonyl O-ethyl S-(1-methylpropyl)phosphoroamidothioate
N-p-chlorobenzyl N-hydrogenthiocarbonyl O-ethyl S-(1-methylpropyl)phosphoroamidodithioate
N-p-chlorobenzyl N-hydrogencarbonyl O-ethyl S-(1-methylpropyl)phosphoroamidodithioate
N-(5-phenyl-1-pentyl)N-hydrogencarbonyl O-ethyl S-(1-methylpropyl)phosphoroamidodithioate
N-(5-phenyl-1-pentyl)N-hydrogenthiocarbonyl O-ethyl S-(1-methylpropyl)phosphoroamidothioate
N-(5-phenyl-1-pentyl)N-hydrogenthiocarbonyl O-ethyl S-(1-methylpropyl)phosphoroamidodithioate
N-methyl N-hydrogencarbonyl-O-propyl S-(1-methylpropyl)phosphoroamidodithioate
N-methyl N-hydrogenthiocarbonyl O-propyl S-(1-methylpropyl)phosphoroamidothioate
N-methyl N-hydrogenthiocarbonyl O-propyl S-(1-methylpropyl)phosphoroamidodithioate
N-methyl N-hydrogenthiocarbonyl O-n-butyl S-(1-methylpropyl)phosphoroamidothioate
N-methyl N-hydrogenthiocarbonyl O-n-butyl S-(1-methylpropyl)phosphoroamidodithioate
N-methyl N-hydrogencarbonyl O-n-butyl S-(1-methylpropyl)phosphoroamidodithioate
N-methyl N-hydrogencarbonyl O-(2,2,2-trifluoroethyl)S-(1-methylpropyl)phosphoroamidodithioate
N-methyl N-hydrogenthiocarbonyl O-(2,2,2-trifluoroethyl)S-(1-methylpropyl)phosphoroamidothioate N-methyl N-hydrogenthiocarbonyl O-(2,2,2-trifluoroethyl)S-1-methylpropyl)phosphoroamidodithioate N-methyl N-hydrogencarbonyl O-allyl S-(1-methylpropyl)phosphoroamidodithioate N-methyl N-hydrogenthiocarbonyl O-allyl S-(1-methylpropyl)phosphoroamidodithioate N-methyl N-hydrogenthiocarobnyl O-allyl S-(1-methylpropyl)phosphoroamidothioate N-methyl N-hydrogenthiocarbonyl O-(3-butenyl)S-(1-methylpropyl)phosphoroamidothioate N-methyl N-hydrogenthiocarobnyl O-(3-butenyl)S-(1-methylpropyl)phosphoroamidodithioate N-methyl N-hydrogencarbonyl O-(3-butenyl)S-(1-methylpropyl)phosphoroamidodithioate N-methyl N-hydrogencarbonyl O-propargyl S-(1-methylpropyl)phosphoroamidodithioate N-methyl N-hydrogenthiocarbonyl O-propargyl S-(1-methylpropyl)phosphoroamidothioate N-methyl N-hydrogenthiocarbonyl O-propargyl S-(1-methylpropyl)phosphoroamidodithioate N-methyl N-hydrogencarbonyl O-(3-hexyn-1-yl)S-(1-methylpropyl)phosphoroamidodithioate N-methyl N-hydrogenthiocarbonyl O-(3-hexyn-1-yl)S-(1-methylpropyl)phosphoroamidodithioate N-methyl N-hydrogencarbonyl O-phenyl S-(1-methylpropyl)phosphoroamidodithioate N-methyl N-hydrogenthiocarbonyl O-phenyl S-(1-methylpropyl)phosphoroamidothioate N-methyl N-hydrogenthiocarbonyl O-pheny S-(1methylpropyl)phosphoroamidodithioate N-methyl N-hydrogencarbonyl O-(2-phenylethyl)S-(1-methylpropyl)phosphoroamidodithioate N-methyl N-hydrogenthiocarbonyl O-(2-phenylethyl)S-(1-methylpropyl)phosphoroamidothioate N-methyl N-hydrogenthiocarbonyl O-(2-phenylethyl S-(1-methylpropyl)phosphoroamidodithioate S,S'-dibutyl N-hydrogenthiocarbonyl N-methyl phosphoroamidodithioate N-hydrogencarbonyl N,S-dimethyl S'-(1-methylpropyl)phosphoroamidotrithioate N-methylthiocarbonyl N,S,S'-tripropyl phosphoroamidodithioate S-ethyl N-heptyl S'-propyl N-trifluoromethylcarbonyl phosphoroamidotrithioate S-methyl S'-pentyl N-propyl N-propoxymethylthiocarbonyl phosphoroamidodithioate S-ethyl S'-(2-hexenyl)N-methyl N-trifluoromethylthiocarbonyl phosphoroamidotrithioate N-ethyl S-methyl S'-(2-propenyl)N-trifluoromethyl phosphoroamidotrithioate N-ethyl N-hydrogenthiocarbonyl S-methyl S'-(1-methylpropyl)phosphoroamidodithioate N-ethyl N-hydrogenthiocarbonyl S-(1-methylpropyl)S'-(2-propynyl)phosphoroamidotrithioate N-ethyl S-(2-hexynyl)N-hydrogencarbonyl S'-(1-methylpropyl)phosphoroamidotrithioate S-(2-fluorobutyl)N-hydrogenthiocarbonyl N-methyl S'-(1-methylethyl)phosphoroamidodithioate N-methylcarbonyl S-phenyl N,S'-dipropyl phosphoroamidotrithioate S-benzyl S'-(1-ethylpropyl)N-hydrogenthiocarbonyl N-methyl phosphorotriamidothiate S-butyl N-ethyl N-methylcarbonyl S'-(5-phenylpentyl)phosphoroamidotrithioate S-butyl N-methylthiocarbonyl N-(2-propenyl)S'-propyl phosphoroamidodithioate N-(3-hexenyl)N-hydrogencarbonyl S,S'-dipropyl phosphoroamidotrithioate N-(3-hexynyl)N-hydrogenthiocarbonyl S-methyl S'-(1-methylpropyl)phosphoroamidodithioate S-ethyl N,S'-di-(3-propynyl)N-trifluoromethylthiocarbonyl phosphoroamidodithioate N-benzyl N-hydrogenthiocarbonyl S,S'-dipropyl phosphoroamidotrithioate N-(carbomethoxymethyl)-N-hydrogencarbonyl O-ethyl-S-(1-methylpropyl)phosphoroamidothioate N-(carboethoxymethyl)-N-hydrogencarbonyl-O-ethyl-S-(1-methylpropyl)phosphoroamidodithioate N-(cyanomethyl)-N-hydrogencarbonyl-O-ethyl-S-(1methylpropyl)phosphoroamidodithioate N-(methoxymethyl)-N-hydrogencarbonyl-O-ethyl-S-(1-methylpropyl)phosphoroamidothioate N-(methylthiomethyl)-N-hydrogencarbonyl-O-ethyl-S-(1-methylpropyl)phosphoroamidodithioate N-benzyl-N-hydrogencarbonyl-O-ethyl-S-(1-methylpropyl)phosphoroamidothioate N-butyl-N-hydrogencarbonyl-O-ethyl-S-(1-methylpropyl)phosphoroamidothioate N-4-fluorobenzyl-N-hydrogencarbonyl-O-ethyl-S-(1-methylpropyl)phosphoroamidodithioate N-3-methoxybenzyl-N-hydrogencarbonyl-O-ethyl-S-(1-methylpropyl)phosphoroamidodithioate N-3-trifluoromethylbenzyl-N-hydrogencarbonyl-O-ethyl-S-(1-methylpropyl)phosphoroamidodithioate N-4-chlorophenylthiomethyl-N-hydrogencarbonyl-O-ethyl-S-(1-methylpropyl)phosphoroamidodithioate N-3-phenyl-2-butenyl-N-hydrogencarbonyl-O-ethyl-S-(1methylpropyl)phosphoroamidodithioate N-1-methylbenzyl-N-hydrogencarbonyl-O-ethyl-S-(1-methylpropyl)phosphoroamidodithioate N-4-nitrobenzyl-N-hydrogencarbonyl-O-ethyl-S-(1-methylpropyl)phosphoroamidothioate N-4-cyanobenzyl-N-hydrogencarbonyl-O-ethyl-S-(1-methylpropyl)phosphoroamidothioate N-phenyl-N-hydrogencarbonyl-O-ethyl-S-(1methylpropyl)phosphoroamidodithioate N-4-chlorophenoxymethyl-N-hydrogencarbonyl-O-ethyl-S-(1-methylpropyl)phosphoroamidodithioate N-1-naphthylmethyl-N-hydrogencarbonyl-O-ethyl-S-(1-methylpropyl)phosphoroamidodithioate N-2-bromobenzyl-N-hydrogencarbonyl-O-ethyl-S-(1methylpropyl)phosphoroamidodithioate N-2-chloro-6-fluorobenzyl-N-hydrogencarbonyl-O-ethyl-S-(1-methylpropyl)phosphoroamidodithioate N-4-methylthiobenzyl-N-hydrogencarbonyl-O-ethyl-S-(1-methylpropyl)phosphoroamidodithioate N-benzyl-N-hydrogencarbonyl-O-ethyl-S-(1-methylpropyl)phosphoroamidothioate N-2-chloro-6-fluorobenzyl-O-ethyl-S-(1-methylpropyl)phosphoroamidothioate N-3-fluorobenzyl-N-hydrogencarbonyl-O-ethyl-S-(1-methylpropyl)phosphoroamidothioate N-2-fluorobenzyl-N-hydrogencarbonyl-O-ethyl-S-(1-methylpropyl)phosphoroamidothioate N-3-cyanobenzyl-N-hydrogencarbonyl-O-ethyl-S-(1methylpropyl)phosphoroamidothioate N-3-nitrobenzyl-N-hydrogencarbonyl-O-ethyl-S-(1-methylpropyl)phosphoroamidothioate The method of controlling arthropods, including insects, nematodes, acarids, other pests, and fungi, according to the invention, comprises applying directly to the insects, nematodes, acarids, other pests and fungi or to the loci to be freed or protected from attack by the arthropods—insects, nematodes, acarids, other pests and fungi—an arthropodocidally effective amount of an active compound having the formula (I) defined hereinabove except that X, Y and Z are independently O or S.

In one preferred aspect, the method of the invention comprises applying on or in the soil an arthropodocidally or pesticidally or fungicidally effective amount of the active compound having the formula (I) above wherein:

$R^1$ is methyl, ethyl, 2,2,2-trifluoroethyl, phenyl or benzyl;

$R^2$ is unsubstituted straight or branched chain ($C_3$-$C_5$)alkyl, phenyl or benzyl;

$R^3$ is hydrogen;

$R^4$ is methyl, ethyl, n—propyl, propenyl, or unsubstituted or substituted benzyl; and X, Y and Z are, independently, O or S.

The following compounds are illustrative of the more preferred group of compounds useful by soil application techniques:

($H_5C_2O$)P(O)(S—n—$C_3H_7$)(N($C_2H_5$)(CHO));
($H_5C_2O$)P(S)(S—sec—$C_4H_9$)(N($C_2H_5$)(CHO));
($H_5C_2O$)P(S)(S—sec—$C_4H_9$)(N($C_2H_5$)(CHS));
($H_2C_2O$)P(O)(S—n—$C_3H_7$)(N($CH_3$)(CHO));
($H_2C_2O$)P(O)(S—n—$C_3H_7$)(N($CH_3$)(CHS));
($H_5C_2O$)P(S) (S—n—$C_3H_7$)(N($CH_3$)(CHO));
($H_5C_2O$)P(S)(S—n—$C_3H_7$)(N($CH_3$)(CHS))
($H_5C_2O$)P(O)(S—sec—$C_4H_9$)(N($CH_3$)(CHS))
($H_5C_2O$)P(S)(S—sec—$C_4H_9$)(N($CH_2CF_3$)(CHO))
($H_5C_2O$)P(S)(S—sec—$C_4H_9$)(N($CH_2CH=CH_2$)(CHO)); and
($H_5C_2O$)P(O)(S—3—pentyl)(N($C_2H_5$)(CHS)).

Especially preferred the method of the invention are the following compounds:

($H_5C_2O$)P(S)(S—sec—$C_4H_9$)(N($C_2H_5$)(CHO));
($H_5C_2O$)P(S)(S—sec—$C_4H_9$)(N($C_2H_5$)(CHS)); and
($H_5C_2O$)P(S)(S—sec—$C_4H_9$)(N($CH_3$)(CHO)).

In another preferred aspect, the method of the invention comprises applying to agricultural plants for foliar application techniques, an arthropodically or pesticidally or fungicidally effective amount of the active compound having the formula (I) above wherein:

$R^1$ is methyl, ethyl, 2,2,2-trifluoromethyl, phenyl or benzyl;

$R^2$ is unsubsitutued straight or branched chain ($C_3$-$C_5$)alkyl, phenyl, or benzyl;

$R^3$ is hydrogen;

$R^4$ is unsubstituted or substituted alkyl or unsubstituted or substituted benzyl; and X, Y, and Z are each O.

The following compounds are illustrative of the more preferred groups of compounds useful by foliar application techniques:

($H_5C_2O$)P(S)(S—sec—$C_4H_9$)(N($CH_2C_6H_4CN$—4)(CHO))
($H_5C_2O$)P(S)(S—sec—$C_4H_9$ )(N($CH_2C_6H_4F$—4)(CHO))

Especially preferred n the foliar application method of the invention are the compounds:

($H_5C_2O$)P(S)(S—sec—$C_4H_9$)(N($CH_2C_6H_4CN$—4)(CHO))
($H_5C_2O$)P(S)(S—sec—$C_4H_9$)(N($CH_2C_6H_4NO_2$—4)(CHO))

The compounds useful according to this invention can be obtained by several reaction sequences. One method for the preparation of hydrogencarbonyl and hydrogenthiocarbonyl phosphoroamido(di)thioates involves conversion of S-alkyl phosphorodichlorothioates to the products in four or five steps as is illustrated by the following reaction scheme:

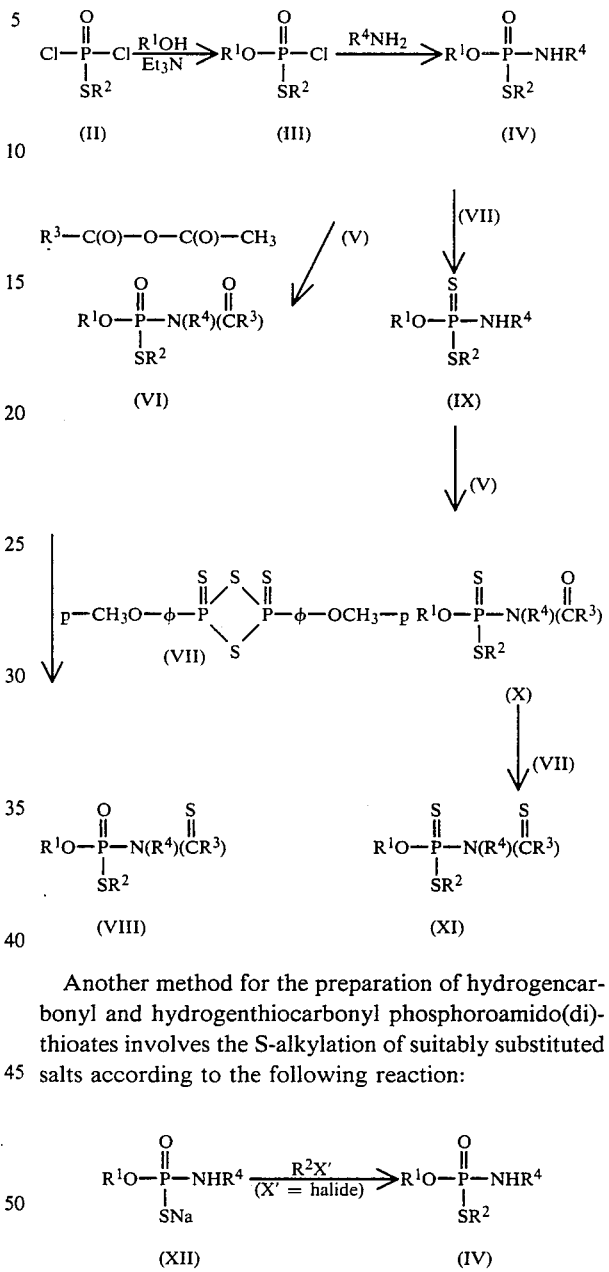

Another method for the preparation of hydrogencarbonyl and hydrogenthiocarbonyl phosphoroamido(di)thioates involves the S-alkylation of suitably substituted salts according to the following reaction:

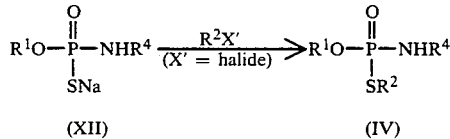

The product of this alkylation reaction having the formula (IV) can then be further treated as illustrated in the reaction scheme set forth above to obtain the new compounds of the invention having the formula (VIII) and (XI).

Still another method for the preparaton of hydrogencarbonyl and hydrogenthiocarbonyl phosphoroamido(di)thioates involves the reaction of diethyl chlorophosphite with a suitably substituted sulfenyl halide to obtain an intermediate O,S-disubstituted phosphorochloridothioate, corresponding to formula (III), designated below by the formula number (III'), in the reaction scheme set forth above, as follows:

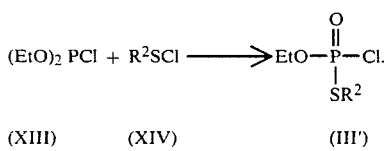

(XIII)   (XIV)   (III')

Intermediate (III') can be further reacted as set forth in the reaction scheme illustrated above to obtain the desired end products.

Yet another method for the preparation of hydrogencarbonyl and hydrogenthiocarbonyl phosphoroamido(di)thioates involves the N-alkylation in the presence of a suitable base of a hydrogencarbonyl phosphoroamido(di)thioate according to the following reaction:

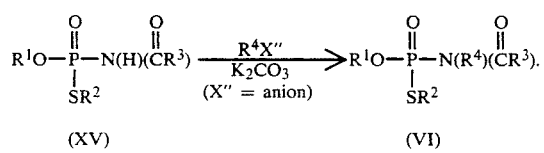

(XV)   (VI)

The product of this reaction having the formula (VI) can be further reacted as set forth in the reaction scheme illustrated above to obtain the hydrogenthiocarbonyl phosphoroamido(di)thioate compound having the formula (VIII).

The S,S-dialkyl phosphoroamidodithioates of the invention can be prepared according to the following sequence:

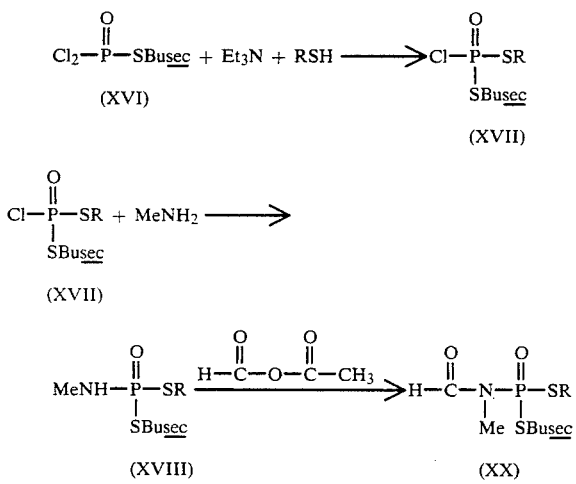

For use as pesticides, the compounds of this invention can be used as solutions, suspensions, or mixtures, in organic solvents or formulations. For example, they can be formulated as wettable powders, emulsifiable concentrates, dusts, granular formulations or flowable emulsifiable concentrates. In such formulations, the compounds of this invention are present at a concentration of about 0.00001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers Annual."

By "agronimically acceptable carrier" is meant any substance which can be utilized to dissolve, disperse or diffuse the chemical incorporated therein without impairing the effectiveness of the toxic agent and which does not create permanent damage to such environment as soil, equipment, and agronomic crops when utilized according to recommendations.

The compounds of this invention can be taken up on or mixed with a finely particled solid carrier, as for example, clays, inorganic silicates, carbonates, and silicas. Organic carriers can also be employed.

Dust concentrates are commonly made wherein compounds are present in the range of about 20 to 80%. For ultimate applications, these concentrates are normally extended with additional solid to given an active ingredient content of from 1 to about 20%. Granular formulations are being made using a granular or pelletized form of carrier, such as granular clays, vermiculite, charcoal or corn cobs, and may contain the active ingredient from about 1 to about 25% by weight.

Wettable powder formulations are made by incorporating the compounds of this invention in an inert, finely divided solid carrier along with a surfactant which can be one or more elulsifying, wetting, dispersing, or spreading agents or a blend of these. The compounds are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such material as glycerol mannitan laurate and a condensate of polygylcerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the compounds of this invention onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the compounds of this invention in an agronomically acceptable organic solvent and adding a solvent-soluble emulsifying agent. Suitable solvents are usually water-immiscible and can be found in the hydrocarbon, chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or non-ionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose of such application, the compound being utilized, the frequency of dissemination, and the like.

Many of the above formulations can be utilized on animals for the control of parasites.

For use as arthropodicides, e.g. acaricides and insecticides, dilute sprays can be applied at concentrations of about 0.01 to about 20 pounds of the active ingredients per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists.

For use as a nematocide or as a soil insecticide, the compounds can be applied as a dilute liquid preparation or as a solid formulation, preferably a granular formulation, by broadcasting, side-dressing, introduction into the seed furrow, soil incorporation, or seed treatment. The application rate can be from about 1 to about 50 pounds per acre of active ingredient and for economic reasons, preferably from about 1 to about 25 pounds per acre.

For use as a fungicide, the organophosphorothiolate or phosphorodithioate can be applied by methods commonly employed, such as conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 to about 50 pounds per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 pounds per acre. As a foliar fungicide, the toxicant is usually applied to growing plants at a rate of about 0.25 to about 10 lbs. per acre.

The compounds of this invention can be utilized as the sole pesticidal agents or they can be employed in conjunction with other bactericides, fungicides, herbicides, insecticides, acaricides, and comparable pesticides.

The following examples are presented to illustrate but a few embodiments of the invention and are not to be constructed as limiting in scope. All parts and percentages are by weight unless otherwise indicated.

EXPERIMENTAL SECTION

Example 1: N-ethyl N-hydrocgencarbonyl O-ethyl S-(1-methylpropyl)phosphoroamidodithioates A solution of N-ethyl O-ethyl S-(1-methylpropyl)-phosphoroamidodithioate, 120.5 g (0.50 mol), in 750 ml of dry tetrahydrofuran (THF) is cooled to (−) 78° C. while being maintained under a nitrogen atmosphere. To this there is added a hexane solution, 229 ml, containing butyllithium (0.55 mol). The resulting reaction mixture is stirred for about 0.25 hr and to this there is then added all-at-once acetic-formic anhydride (0.55 mol). The resulting reaction mixture is then warmed to 0° C. over period of 2 hrs and filtered through a celite filter pad. The solvent and excess acetic-formic anhydride and acetic acid by-product are removed from the filtrate by distillation under reduced pressure to afford 118.6 g (88% of theory) of product as a clear yellow oil.

Examples 2–6 are prepared by a procedure analogous to that of Example 1 except that acetic anhydride or trifluoroacetic anhydride are substituted for acetic-formic anhydride in several of these Examples:

Example 2: N-ethyl N-methylcarbonyl O-ethyl S-(1-methylpropyl)phosphoroamidodithioate Example 3: N-ethyl N-trifluoromethylcarbonyl O-ethyl S-(1-methylpropyl)phosphoroamidodithioate Example 4: N-ethyl N-hydrogencarbonyl O-ethyl s-methyl phosphoroamidodithioate Example 5: N-ethyl N-hydrogencarbonyl O-ethyl S-(5-methyl-1,2,4-oxadiazolymethyl)phosphoroamidodithioate Example 6: N-(2,2,2-trifluoroethyl N-hydrogencarbonyl O-ethyl S-(1-methylpropyl)phosphoroamidodithioate.

Example 7: N-methyl N-hydrogencarbonyl O-ethyl S-(1-methylpropyl)phosphoroamidodithoate Formic acid, 4.48 g (0.105 mol) and acetic anhydride, 7.96 g (0.078 mol) are mixed in a flask at room temperature and allowed to stand for 0.5 hr. After cooling this mixture in an ice bath, there is added N-methyl O-ethyl S-(1-methylpropyl phosphoroamidodithioate, 12 g (0.0527 mol). The resulting reaction mixture is warmed to room temperature and stirred for 1 day at room temperature. Removal of excess acetic-formic anhydride and acetic acid by-product from the resulting reaction mixture by distillation under reduced pressure affords 13.4 g (100% of theory) of product as a colorless oil.

Examples 8–15 and 49–65 are prepared by a procedure analogous to that of Example 7:

Example 8: N-methyl N-hydrogencarbonyl O-ethyl S-ethyl phosphoroamidodithioate

Example 9: N-methyl N-hydrogencarbonyl O-methyl S-(1-methylpropyl)phosphoroamidothioate Example 10: N-methyl N-hydrogencarbonyl O-m-trifluoromethylphenyl S-(1-methylpropyl)phosphoroamidodithioate Example 11: N-methyl N-hydrogencarbonyl O-ethyl S-propyl phosphoroamidodithioate Example 12: N-methyl N-hydrogencarbonyl O-ethyl S-isopropyl phosphoroamidodithioate Example 13: N-methyl N-hydrogencarbonyl O-ethyl S-tert-butyl phosphoroamidodithioate Example 14: N-methyl N-hydrogencarbonyl O-ethyl S-(3-pentyl)phosphoroamidodithioate Example 15: N-methyl N-hydrogencarbonyl O-ethyl S-allyl phosophoroamidodithioate Example 16: N-ethyl N-hydrogenthiocarbonyl O-ethyl S-(1-methylpropyl)phosphoroamidodithioate A solution of N-ethyl N-hydrogencarbonyl O-ethyl S-(1-methylpropyl)phosphoroamidodithioate, 65 g (0.24 mol), and 2,4-bis-(4-methoxyphenyl)-2,4-dithioxo-1,3,2,4-dithiadiphosphetan, 60.7 g (0.15 mol) in 750 ml of 1,2-dimethoxyethane is stirred and heated at reflux temperature for about 2 hr. The resulting clear yellow solution is cooled and the solvent is removed by distillation under reduced pressure. Hexane, 1L, is added to the residue and the resulting mixture is first stirred vigorously for 0.25 hr and then allowed to stand for 0.25 hr. The hexane layer is decanted-off and the hexane is removed from this portion by distillation under reduced pressure to afford 42 g (61% of theory) of product as a yellow oil. The product can be further purified by eluting a hexane solution of the product on a chromatographic column using Bio-Sil A ® (a silica gel chromatography support product available from Biorad Laboratories).

Examples 17–26 and 66–94 are prepared by a procedure analogous to that of Example 16:

Example 17: N-methylthiomethyl N-hydrogenthiocarbonyl O-ethyl S-(1-methylpropyl)phosphoroamidodithioate Example 18: N-ethyl N-hydrogenthiocarbonyl O-ethyl S-methyl phosphoroamidodithioate Example 19: N-methyl N-hydrogenthiocarbonyl O-ethyl S-n-propyl phosphoroamidodithoate Example 20: N-methyl N-hydrogenthiocarbonyl O-ethyl S-isopropyl phosphoroamidodithioate Example 21: N-hydrogenthiocarbonyl O-ethyl S-(1-methylpropyl)phosphoroamidodithioate Example 22: N-methyl N-hydrogenthiocarbonyl O-ethyl S-(1-methylpropyl)phosphoroamidodithioate Example 23: N-allyl N-hydrogenthiocarbonyl O-ethyl S-(1-methylpropyl)phosphoramidodithioate Example 24: N-methyl N-hydrogenthiocarbonyl O-ethyl S-tert-butyl phosphoroamidodithioate Example 25: N-methyl N-hydrogenthiocarbonyl O-ethyl S-(3-pentyl)phosphoroamidodithioate Example 26: N-methyl N-hydrogenthiocarbonyl O-ethyl s-(1-methylpropyl)phosphoroamidothioate In Examples 27–37 and 95–120, a phosphoroamidothioate precursor is substituted for a phosphoroamidodithioate precursor used in Example 16.

Example 27: N-propyl N-hydrogenthiocarbonyl O-ethyl S-(1-methylpropyl)phosphoroamidothioate Example 28: N-butyl N-hydrogenthiocarbonyl O-ethyl S-(1-methylpropyl)phosphoroamidothioate Example 29: N-benzyl N-hydrogenthiocarbonyl O-ethyl S-(1-methylpropyl)phosphoroamidothioate Example 30: N-methylthiomethyl N-hydrogenthiocarbonyl O-ethyl S-(1-methylpropyl)phosphoroamidothioate Example 31: N-methyl N-hydrogenthiocarbonyl O-ethyl S-ethyl phosphoroamidothioate Example 32: N-methyl N-hydrogenthiocarbonyl O-ethyl S-n-propyl phosphoroamidothioate Example 33: N-methyl N-hydrogenthiocarbonyl O-ethyl S-isopropyl phosphoroamidothioate Example 34: N-allyl N-hydrogenthiocarbonyl O-ethyl S-(1-methylpropyl)phosphoroamidothioate Example 35: N-methyl N-hydrogenthiocarobnyl O-ethyl S-(3-pentyl)phosphoroamidothioate Example 36: N-ethyl N-hydrogenthiocarbonyl O-ethyl S-(3-pentyl)phosphoroamidothioate Example 37: N-allyl N-hydrogencarbonyl O-ethyl S-(1-methylpropyl)phosphoroamidodithioate To a solution of N-hydrogencarbonyl O-ethyl S-(1-methylpropyl)phosphoroamidodithioate, 11.2 g (0.46 mol), and ally bromide, 9.4 g (0.056 mol), in 100 ml of methyl ethyl ketone is added powdered K$_2$CO$_3$, 8.32 g (0.060 mol). The resulting suspension is stirred in ambient temperature for 24 hr. and then filtered. The solvent is removed from the filtrate by distillation under reduced pressure to afford 9.1 g (87% of theory) of product as a pale yellow oil. Further purification can be effected by high pressure liquid chromatography (HPLC) techniques.

Examples 38–41 and 121–146 are prepared by a procedure analogous to that of Example 37:

Example 38: N-propargyl N-hydrogencarbonyl O-ethyl S-(1-methylpropyl)phosphoroamidodithioate Example 39: N-methylthiomethyl N-hydrogencarbonyl O-ethyl S-(1-methylpropyl)phosphoroamidodithioate Example 40: N-butyl N-hydrogencarbonyl O-ethyl S-(1-methylpropyl)phosphoroamidodithioate Example 43: Preparation of

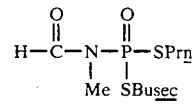

N-Hydrogencarbonyl N-methyl S-(1-methylpropyl)S'-propyl phosphoroamidodithioate

STEP 1

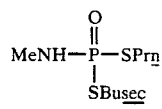

Preparation of N-methyl S-(1-methylpropyl)S'-propyl phosphoroamidothioate

A solution of n-propyl mercaptan (23.63 g., 0.311 moles) and triethylamine (31.41 g., 0.311 moles) in 100 ml of tetrahydrofuran is added dropwise to an ice-cooled solution of S-(1-methylpropyl)phosphorodichloridothioate (64.4 g., 0.311 moles) in 200 ml of THF. The reaction was stirred 1 hr. at R.T., then methylamine (19.3 g., 0.622 moles) is bubbled into the reaction mixture. The reaction is diluted with ether, filtered through celite to remove the triethylamine hydrochloride and methylamine hydrochloride, and evaporated to give 75 grams of product as an oil which is purified by preparative high pressure liquid chromatography (HPLC), using two prepPak 500 silica gel columns in series.

STEP 2

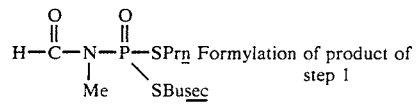

Formic acid, 97%, (1.04 g., 0.026 moles) is added to acetic anhydride (2.10 g., 0.0206 moles) and stirred 15 min. at room temperature. The resulting formic-acetic anhydride is added to N-methyl S-(1-methylpropyl)S'-(propyl)phosphoramidodithioate (2.5 g., 0.0103 mole) and three drops of 85% phosphoric acid. The reaction is stirred 24 hours at room temperature and evaporated under high vacuum to remove acetic acid and formic-acetic anhydride, leaving 2.1 g. of material. Purification by preparative HPLC gave 0.5 of product as an oil.

Example 147: N-methylthiomethyl N-hydrogencarbonyl O-ethyl S-(1-methylpropyl)phosphoroamidothioate To a solution of N-hydrogencarbonyl O-ethyl S-(1-methyl-propyl)phosphoroamidothioate, 4.0 g (0.018 mol) and chloromethyl methyl sulfide, 1.84 g (0.019 mol) in 100 ml of methyl ethyl ketone is added powdered K$_2$CO$_3$, 3.73 g (0.027 mol). The resulting suspension is stirred in ambient temperature for 24 hr. and then filtered. The solvent is removed from the filtrate by distillation under reduced pressure to afford 4.3 g (84% of theory) of product as a pale yellow oil. Further purification can be effected by high pressure liquid chromatography (HPLC) techniques.

Examples 148–179 are prepared by a procedure analogous to that of Example 147.

Table I below depicts the various substituent groups in the illustrative compounds made according to formula (I) above:

TABLE I

Tabular List of Substituents in Examples $$R^1Z\underset{\underset{SR^2}{|}}{\overset{\overset{X}{\|}}{P}}-N(R^4)(CR^3)\overset{\overset{Y}{\|}}{}$$

| Example | X | Y | Z | $R^1$ | $R^2$ | $R^3$ | $R^4$ |
|---|---|---|---|---|---|---|---|
| 1 | S | O | O | $C_2H_5$ | s-$C_4H_9$ | H | $C_2H_5$ |
| 2 | S | O | O | $C_2H_5$ | s-$C_4H_9$ | $CH_3$ | $C_2H_5$ |
| 3 | S | O | O | $C_2H_5$ | s-$C_4H_9$ | $CF_3$ | $C_2H_5$ |
| 4 | S | O | O | $C_2H_5$ | $CH_3$ | H | $C_2H_5$ |
| 5 | S | O | O | $C_2H_5$ | (cyclic structure with O, N, N, CH₃, CH₂) | H | $C_2H_5$ |
| 6 | S | O | O | $C_2H_5$ | s-$C_4H_9$ | H | $CH_2CF_3$ |
| 7 | S | O | O | $C_2H_5$ | s-$C_4H_9$ | H | $CH_3$ |
| 8 | S | O | O | $C_2H_5$ | $C_2H_5$ | H | $CH_3$ |
| 9 | S | O | O | $CH_3$ | s-$C_4H_9$ | H | $CH_3$ |
| 10 | S | O | O | m-$CF_3$—$C_6H_4$ | s-$C_4H_9$ | H | $CH_3$ |
| 11 | S | O | O | $C_2H_5$ | n-$C_3H_7$ | H | $CH_3$ |
| 12 | S | O | O | $C_2H_5$ | i-$C_3H_7$ | H | $CH_3$ |
| 13 | S | O | O | $C_2H_5$ | t-$C_4H_9$ | H | $CH_3$ |
| 14 | S | O | O | $C_2H_5$ | $CH(C_2H_5)_2$ | H | $CH_3$ |
| 15 | S | O | O | $C_2H_5$ | $CH_2CH=CH_2$ | H | $CH_3$ |
| 16 | S | S | O | $C_2H_5$ | s-$C_4H_9$ | H | $C_2H_5$ |
| 17 | S | S | O | $C_2H_5$ | s-$C_4H_9$ | H | $CH_2SCH_3$ |
| 18 | S | S | O | $C_2H_5$ | $CH_3$ | H | $C_2H_5$ |
| 19 | S | S | O | $C_2H_5$ | n-$C_3H_7$ | H | $CH_3$ |
| 20 | S | S | O | $C_2H_5$ | i-$C_3H_7$ | H | $CH_3$ |
| 21 | S | S | O | $C_2H_5$ | s-$C_4H_9$ | H | H |
| 22 | S | S | O | $C_2H_5$ | s-$C_4H_9$ | H | $CH_3$ |
| 23 | S | S | O | $C_2H_5$ | s-$C_4H_9$ | H | $CH_2CH=CH_2$ |
| 24 | S | S | O | $C_2H_5$ | t-$C_4H_9$ | H | $CH_3$ |
| 25 | S | S | O | $C_2H_5$ | $CH(C_2H_5)_2$ | H | $CH_3$ |
| 26 | O | S | O | $C_2H_5$ | s-$C_4H_9$ | H | $CH_3$ |
| 27 | O | S | O | $C_2H_5$ | s-$C_4H_9$ | H | n-$C_3H_7$ |
| 28 | O | S | O | $C_2H_5$ | s-$C_4H_9$ | H | n-$C_4H_9$ |
| 29 | O | S | O | $C_2H_5$ | s-$C_4H_9$ | H | $CH_2C_6H_5$ |
| 30 | O | S | O | $C_2H_5$ | s-$C_4H_9$ | H | $CH_2SCH_3$ |
| 31 | O | S | O | $C_2H_5$ | $C_2H_5$ | H | $CH_3$ |
| 32 | O | S | O | $C_2H_5$ | n-$C_3H_7$ | H | $CH_3$ |
| 33 | O | S | O | $C_2H_5$ | i-$C_3H_7$ | H | $CH_3$ |
| 34 | O | S | O | $C_2H_5$ | s-$C_4H_9$ | H | $CH_2CH=CH_2$ |
| 35 | O | S | O | $C_2H_5$ | $CH(C_2H_5)_2$ | H | $CH_3$ |
| 36 | O | S | O | $C_2H_5$ | $CH(C_2H_5)_2$ | H | $C_2H_5$ |
| 37 | S | O | O | $C_2H_5$ | s-$C_4H_9$ | H | $CH_2CH=CH_2$ |
| 38 | S | O | O | $C_2H_5$ | s-$C_4H_9$ | H | $CH_2C\equiv CH$ |
| 39 | S | O | O | $C_2H_5$ | s-$C_4H_9$ | H | $CH_2SCH_3$ |
| 40 | S | O | O | $C_2H_5$ | s-$C_4H_9$ | H | n-$C_4H_9$ |
| 41 | S | O | O | $C_2H_5$ | s-$C_4H_9$ | H | H |
| 42 | S | O | O | $C_2H_5$ | s-$C_4H_9$ | H | $CH_2CN$ |
| 43 | O | O | S | n-$C_3H_7$ | s-$C_4H_9$ | H | $CH_3$ |
| 44 | O | O | S | s-$C_4H_9$ | s-$C_4H_9$ | H | $CH_3$ |
| 45 | S | O | O | $C_2H_5$ | s-$C_4H_9$ | H | H |
| 46 | S | O | O | $C_2H_5$ | s-$C_4H_9$ | H | $CH_2CN$ |
| 47 | O | S | O | n-$C_3H_7$ | s-$C_4H_3$ | H | $CH_3$ |
| 48 | O | S | O | s-$C_4H_9$ | s-$C_4H_9$ | H | $CH_3$ |
| 49 | S | O | O | $C_2H_5$ | i-$C_4H_9$ | H | $CH_3$ |
| 50 | S | O | O | $C_2H_5$ | n-$C_4H_9$ | H | $CH_3$ |
| 51 | S | O | O | $C_2H_5$ | i-$C_5H_{11}$ | H | $CH_3$ |
| 52 | S | O | O | $C_2H_5$ | $CH_2CH(CH_3)CH_2CH_3$ | H | $CH_3$ |
| 53 | S | O | O | $C_2H_5$ | s-$C_5H_{11}$ | H | $CH_3$ |
| 54 | S | O | O | $C_2H_5$ | $CH_2CH_2CH=CH_2$ | H | $CH_3$ |
| 55 | S | O | O | $C_2H_5$ | $CH_2CH_2OCH_3$ | H | $CH_3$ |
| 56 | S | O | O | $CH_2CF_3$ | s-$C_4H_9$ | H | $CH_3$ |
| 57 | S | O | O | $C_2H_5$ | $CH(C_2H_5)_2$ | H | $CH_3$ |
| 58 | S | O | O | $C_2H_5$ | n-$C_3H_7$ | H | $C_2H_5$ |
| 59 | S | O | O | $C_2H_5$ | n-$C_3H_7$ | H | H |
| 60 | S | O | O | n-$C_3H_7$ | s-$C_4H_9$ | H | $C_2H_5$ |
| 61 | S | O | O | n-$C_3H_7$ | s-$C_4H_9$ | H | $CH_3$ |
| 62 | S | O | O | $CH_2CF_3$ | s-$C_4H_9$ | H | $C_2H_5$ |

TABLE I-continued

Tabular List of Substituents in Examples $$R^1Z-\overset{\overset{X}{\|}}{\underset{\underset{SR^2}{|}}{P}}-N(R^4)(CR^3)\overset{Y}{\|}$$

| Example | X | Y | Z | $R^1$ | $R^2$ | $R^3$ | $R^4$ |
|---|---|---|---|---|---|---|---|
| 63 | S | O | O | $CH_2CH_2F$ | $s\text{-}C_4H_9$ | H | $CH_3$ |
| 64 | S | O | O | $CH_2CH_2OCH_3$ | $s\text{-}C_4H_9$ | H | $CH_3$ |
| 65 | S | O | O | $CH_2CF_2CF_2H$ | $s\text{-}C_4H_9$ | H | $CH_3$ |
| 66 | S | S | O | $3\text{-}CF_3C_6H_4$ | $s\text{-}C_4H_9$ | H | $CH_3$ |
| 67 | S | S | O | $C_2H_5$ | $s\text{-}C_4H_9$ | H | $CH_2SCH_3$ |
| 68 | S | S | O | $C_2H_5$ | $i\text{-}C_4H_9$ | H | $CH_3$ |
| 69 | S | S | O | $C_2H_5$ | $n\text{-}C_4H_9$ | H | $CH_3$ |
| 70 | S | S | O | $C_2H_5$ | $i\text{-}C_5H_{11}$ | H | $CH_3$ |
| 71 | S | S | O | $C_2H_5$ | $n\text{-}C_5H_{11}$ | H | $CH_3$ |
| 72 | S | S | O | $C_2H_5$ | $CH_2CH(CH_3)CH_2CH_3$ | H | $CH_3$ |
| 73 | S | S | O | $C_2H_5$ | $s\text{-}C_5H_{11}$ | H | $CH_3$ |
| 74 | S | S | O | $C_2H_5$ | $CH_2CH_2CH=CH_2$ | H | $CH_3$ |
| 75 | S | S | O | $C_2H_5$ | $CH_2CH_2OCH_3$ | H | $CH_3$ |
| 76 | S | S | O | $CH_2CF_3$ | $s\text{-}C_4H_9$ | H | $CH_3$ |
| 77 | S | S | O | $n\text{-}C_3H_7$ | $s\text{-}C_4H_9$ | H | $C_2H_5$ |
| 78 | S | S | O | $n\text{-}C_3H_7$ | $s\text{-}C_4H_9$ | H | $CH_3$ |
| 79 | S | S | O | $C_2H_5$ | $s\text{-}C_4H_9$ | H | $CH_2CO_2CH_3$ |
| 80 | S | S | O | $C_2H_5$ | $s\text{-}C_4H_9$ | H | $CH_2C_6H_5$ |
| 81 | S | S | O | $C_2H_5$ | $s\text{-}C_4H_9$ | H | $CH_2C_6H_4F\text{—}4$ |
| 82 | S | S | O | $C_2H_5$ | $s\text{-}C_4H_9$ | H | $CH_2C_6H_4OCH_3\text{—}3$ |
| 83 | S | S | O | $C_2H_5$ | $s\text{-}C_4H_9$ | H | $CH_2C_6H_4CF_3\text{—}3$ |
| 84 | S | S | O | $C_2H_5$ | $s\text{-}C_4H_9$ | H | $CH_2CH_2CH_2Cl$ |
| 85 | S | S | O | $C_2H_5$ | $s\text{-}C_4H_9$ | H | $CH_2SC_6H_4Cl\text{—}4$ |
| 86 | S | S | O | $C_2H_5$ | $s\text{-}C_4H_9$ | H | $CH_2C(Br)=CH_2$ |
| 87 | S | S | O | $C_2H_5$ | $s\text{-}C_4H_9$ | H | $CH_2CH=CHC_6H_5$ |
| 88 | S | S | O | $C_2H_5$ | $s\text{-}C_4H_9$ | H | $CH_2CO_2C_2H_5$ |
| 89 | S | S | O | $C_2H_5$ | $CH_2CH_2OCH_3$ | H | $CH_3$ |
| 90 | S | S | O | $CH_2CF_2CF_2H$ | $s\text{-}C_4H_9$ | H | $CH_3$ |
| 91 | S | S | O | $CH_2CF_3$ | $s\text{-}C_4H_9$ | H | $C_2H_5$ |
| 92 | S | S | O | $C_2H_5$ | $s\text{-}C_4H_9$ | H | $CH_2SC_6H_5$ |
| 93 | S | S | O | $C_2H_5$ | $s\text{-}C_4H_9$ | H | $CH_2CH=CHCH_3$ |
| 94 | S | S | O | $C_2H_5$ | $s\text{-}C_4H_9$ | H | $CH_2C_6H_4NO_2\text{—}4$ |
| 95 | O | S | O | $C_2H_5$ | $s\text{-}C_4H_9$ | H | $CH_2C\equiv CH$ |
| 96 | O | S | O | $CH_2CF_3$ | $s\text{-}C_4H_9$ | H | $CH_3$ |
| 97 | O | S | O | $C_2H_5$ | $CH_2CH=CH_2$ | H | $CH_3$ |
| 98 | O | S | O | $C_2H_5$ | $s\text{-}C_4H_9$ | H | $CH_3$ |
| 99 | O | S | O | $C_2H_5$ | $n\text{-}C_4H_9$ | H | $CH_3$ |
| 100 | O | S | O | $C_2H_5$ | $CH_2CH(CH_3)CH_2CH_3$ | H | $CH_3$ |
| 101 | O | S | O | $C_2H_5$ | $s\text{-}C_5H_{11}$ | H | $CH_3$ |
| 102 | O | S | O | $C_2H_5$ | $s\text{-}C_4H_9$ | H | $C_2H_5$ |
| 103 | O | S | O | $n\text{-}C_3H_7$ | $s\text{-}C_4H_9$ | H | $CH_3$ |
| 104 | O | S | O | $C_2H_5$ | $s\text{-}C_4H_9$ | H | $CH_2C_6H_4F\text{—}4$ |
| 105 | O | S | O | $C_2H_5$ | $s\text{-}C_4H_9$ | H | $CH_2C_6H_4OCH_3\text{—}3$ |
| 106 | O | S | O | $C_2H_5$ | $s\text{-}C_4H_9$ | H | $CH_2C_6H_4CF_3\text{—}3$ |
| 107 | O | S | O | $CH_2CH_2F$ | $s\text{-}C_4H_9$ | H | $CH_3$ |
| 108 | O | S | O | $C_2H_5$ | $s\text{-}C_4H_9$ | H | $CH_2CH=CHCH_3$ |
| 109 | O | S | O | $C_2H_5$ | $C_3H_7$ | H | $CH_2CH=CH_2$ |
| 110 | O | S | O | $C_2H_5$ | $C_3H_7$ | H | $CH_2C\equiv CH$ |
| 111 | O | S | O | $C_2H_5$ | $s\text{-}C_4H_9$ | H | $CH_2C_{10}H_7$ |
| 112 | O | S | O | $C_2H_5$ | $s\text{-}C_4H_9$ | H | $CH_2C_6H_4Br\text{—}2$ |
| 113 | O | S | O | $C_2H_5$ | $s\text{-}C_4H_9$ | H | $CH_2C_6H_3ClF\text{—}2,6$ |
| 113 | O | S | O | $C_2H_5$ | $s\text{-}C_4H_9$ | H | $CH_2C_6H_3ClF\text{—}2,6$ |
| 114 | O | S | O | $C_2H_5$ | $n\text{-}C_3H_7$ | H | $n\text{-}C_3H_7$ |
| 115 | O | S | O | $C_2H_5$ | $n\text{-}C_3H_7$ | H | $n\text{-}C_4H_9$ |
| 116 | O | S | O | $C_2H_5$ | $s\text{-}C_4H_9$ | H | $CH_2C_6H_3CH_3NO_2\text{—}3,4$ |
| 117 | O | S | O | $C_2H_5$ | $s\text{-}C_4H_9$ | H | $CH_2C_6F_5\text{—}2,3,4,5,6$ |
| 118 | O | S | O | $C_2H_5$ | $s\text{-}C_4H_9$ | H | $CH_2C_6H_3Cl_2\text{—}2,6$ |
| 119 | O | S | O | $C_2H_5$ | $n\text{-}C_3H_7$ | H | $CH_2C_6H_5$ |
| 120 | O | S | O | $C_2H_5$ | $n\text{-}C_3H_7$ | H | $CH_2CO_2CH_3$ |
| 121 | S | O | O | $C_2H_5$ | $s\text{-}C_4H_9$ | H | $CH_2CO_2CH_3$ |
| 122 | S | O | O | $C_2H_5$ | $s\text{-}C_4H_9$ | H | $CH_2C_6H_5$ |
| 123 | S | O | O | $C_2H_5$ | $s\text{-}C_4H_9$ | H | $CH_2C_6H_4F\text{—}4$ |
| 124 | S | O | O | $C_2H_5$ | $s\text{-}C_4H_9$ | H | $CH_2C_6H_4OCH_3\text{—}3$ |
| 125 | S | O | O | $C_2H_5$ | $s\text{-}C_4H_9$ | H | $CH_2C_6H_4CF_3\text{—}3$ |
| 126 | S | O | O | $C_2H_5$ | $s\text{-}C_4H_9$ | H | $CH_2CH_2CH_2Cl$ |
| 127 | S | O | O | $C_2H_5$ | $s\text{-}C_4H_9$ | H | $CH_2SC_6H_4Cl\text{—}4$ |
| 128 | S | O | O | $C_2H_5$ | $s\text{-}C_4H_9$ | H | $CH_2C(Br)=CH_2$ |
| 129 | S | O | O | $C_2H_5$ | $s\text{-}C_4H_9$ | H | $CH_2CH=CHC_6H_5$ |
| 130 | S | O | O | $C_2H_5$ | $s\text{-}C_4H_9$ | H | $CH_2CO_2C_2H_5$ |
| 131 | S | O | O | $C_2H_5$ | $n\text{-}C_4H_9$ | H | $CH_2C_6H_4NO_2\text{—}4$ |
| 132 | S | O | O | $C_2H_5$ | $s\text{-}C_4H_9$ | H | $CH_2C_6H_4CN\text{—}4$ |
| 133 | S | O | O | $C_2H_5$ | $s\text{-}C_4H_9$ | H | $CH_2C(O)C_6H_5$ |
| 134 | S | O | O | $C_2H_5$ | $s\text{-}C_4H_9$ | H | $CH_2C_6H_4Br\text{—}2$ |
| 135 | S | O | O | $C_2H_5$ | $s\text{-}C_4H_9$ | H | $CH_2OC_6H_4Cl\text{—}4$ |

TABLE I-continued
Tabular List of Substituents in Examples $$R^1Z-\overset{\overset{X}{\|}}{\underset{\underset{SR^2}{|}}{P}}-N(R^4)(\overset{\overset{Y}{\|}}{C}R^3)$$

| Example | X | Y | Z | R¹ | R² | R³ | R⁴ |
|---|---|---|---|---|---|---|---|
| 136 | S | O | O | $C_2H_5$ | $\underline{s}$-$C_4H_9$ | H | $CH_2C_{10}H_7$ |
| 137 | S | O | O | $C_2H_5$ | $\underline{s}$-$C_4H_9$ | H | $CH_2CH=CHCH_3$ |
| 138 | S | O | O | $C_2H_5$ | $\underline{s}$-$C_4H_9$ | H | $CH_2C_6H_3ClF$—2,6 |
| 139 | S | O | O | $C_2H_5$ | $\underline{s}$-$C_4H_9$ | H | $CH_2C_6F_5$—2,3,4,5,6 |
| 140 | S | O | O | $C_2H_5$ | $\underline{n}$-$C_3H_7$ | H | $\underline{n}$-$C_4H_9$ |
| 141 | S | O | O | $C_2H_5$ | $\underline{n}$-$C_3H_7$ | H | $CH_2C_6H_5$ |
| 142 | S | O | O | $C_2H_5$ | $\underline{n}$-$C_3H_7$ | H | $CH_2CO_2C_2H_5$ |
| 143 | S | O | O | $C_2H_5$ | $\underline{n}$-$C_3H_7$ | H | $CH_2CH_2CH_2Cl$ |
| 144 | S | O | O | $C_2H_5$ | $\underline{s}$-$C_4H_9$ | H | $CH_2C_6H_4OCH_2C_6H_5$ |
| 145 | S | O | O | $C_2H_5$ | $\underline{s}$-$C_4H_9$ | H | 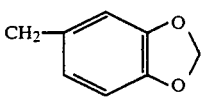 |
| 146 | S | O | O | $C_2H_5$ | $\underline{s}$-$C_4H_9$ | H | $CH_2C(CH_3)=CH_2$ |
| 147 | O | O | O | $C_2H_5$ | $\underline{s}$-$C_4H_9$ | H | $CH_2SCH_3$ |
| 148 | O | O | O | $C_2H_5$ | $\underline{s}$-$C_4H_9$ | H | $CH_2C_6H_5$ |
| 149 | O | O | O | $C_2H_5$ | $\underline{s}$-$C_4H_9$ | H | $CH_2CN$ |
| 150 | O | O | O | $C_2H_5$ | $\underline{s}$-$C_4H_9$ | H | $CH_2OCH_3$ |
| 151 | O | O | O | $C_2H_5$ | $\underline{s}$-$C_4H_9$ | H | $CH_2CH_2CH_2Cl$ |
| 152 | O | O | O | $C_2H_5$ | $\underline{s}$-$C_4H_9$ | H | $CH_2C_6H_4F$—4 |
| 153 | O | O | O | $C_2H_5$ | $\underline{s}$-$C_4H_9$ | H | $CH_2C_6H_4OCH_3$—3 |
| 154 | O | O | O | $C_2H_5$ | $\underline{s}$-$C_4H_9$ | H | $CH_2C_6H_4CF_3$—3 |
| 155 | O | O | O | $C_2H_5$ | $\underline{s}$-$C_4H_9$ | H | $CH_2SC_6H_4Cl$—4 |
| 156 | O | O | O | $C_2H_5$ | $\underline{s}$-$C_4H_9$ | H | $CH_2CH=CHC_6H_5$ |
| 157 | O | O | O | $C_2H_5$ | $\underline{s}$-$C_4H_9$ | H | $CH_2SC_6H_5$ |
| 158 | O | O | O | $C_2H_5$ | $\underline{s}$-$C_4H_9$ | H | $CH_2C_6H_4CH_3$—2 |
| 159 | O | O | O | $C_2H_5$ | $\underline{s}$-$C_4H_9$ | H | $CH_2C_6H_4NO_2$—4 |
| 160 | O | O | O | $C_2H_5$ | $\underline{s}$-$C_4H_9$ | H | $CH_2CH_2CH_2Cl$ |
| 161 | O | O | O | $C_2H_5$ | $\underline{s}$-$C_4H_9$ | H | $CH_2C(O)C_6H_5$ |
| 162 | O | O | O | $C_2H_5$ | $\underline{s}$-$C_4H_9$ | H | $CH_2C_{10}H_7$ |
| 163 | O | O | O | $C_2H_5$ | $\underline{s}$-$C_4H_9$ | H | $CH_2C_6H_4Br$—2 |
| 164 | O | O | O | $C_2H_5$ | $\underline{s}$-$C_4H_9$ | H | $CH_2C_2H_3ClF$—2,6 |
| 165 | O | O | O | $C_2H_5$ | $\underline{s}$-$C_4H_9$ | H | $CH_2C_6F_5$—2,3,4,5,6 |
| 166 | O | O | O | $C_2H_5$ | $\underline{s}$-$C_4H_9$ | H | $CH_2C_6H_3Cl_2$—2,6 |
| 167 | O | O | O | $C_2H_5$ | $\underline{n}$-$C_3H_7$ | H | $CH_2C_6H_5$ |
| 168 | O | O | O | $C_2H_5$ | $\underline{n}$-$C_3H_7$ | H | $CH_2C_6H_4F$—4 |
| 169 | O | O | O | $C_2H_5$ | $\underline{n}$-$C_3H_7$ | H | $CH_2C_6H_3ClF$—2,6 |
| 170 | O | O | O | $CH_2CH_2F$ | $\underline{s}$-$C_4H_9$ | H | $CH_2C_6H_5$ |
| 171 | O | O | O | $CH_2CH_2F$ | $\underline{s}$-$C_4H_9$ | H | $CH_2C_6H_4NO_2$—4 |
| 172 | O | O | O | $C_2H_5$ | $\underline{n}$-$C_3H_7$ | H | $CH_2C_6H_4CF_3$—3 |
| 173 | O | O | O | $C_2H_5$ | $\underline{s}$-$C_4H_9$ | H | $CH_2C_6H(CH_3)_4$—2,3,5,6 |
| 174 | O | O | O | $C_2H_5$ | $\underline{s}$-$C_4H_9$ | H | $CH_2C_6H_4C(O)CH_3$—3 |
| 175 | O | O | O | $C_2H_5$ | $\underline{s}$-$C_4H_9$ | H | $CH_2C_6H_4CH_3$—2 |
| 176 | O | O | O | $C_2H_5$ | $\underline{s}$-$C_4H_9$ | H | $CH_2C_6H_3CH_3NO_2$—3,4 |
| 177 | O | O | O | $C_2H_5$ | $\underline{s}$-$C_4H_9$ | H | $CH_2C_6H_4F$—3 |
| 178 | O | O | O | $C_2H_5$ | $\underline{s}$-$C_4H_9$ | H | $CH_2C_6H_3Cl_2$—3,4 |
| 179 | O | O | O | $C_2H_5$ | $\underline{s}$-$C_4H_9$ | H | $CH_2C_6H_3(CH_3)_2$—2,5 |
| 180 | O | O | O | $C_2H_5$ | $\underline{s}$-$C_4H_9$ | H | $CH_2C_6H_4CN$—4 |

Tables II and III which follow, respectively, set forth the analytical data and nuclear magnetic resonance (nmr) data of representative compounds selected from Table I.

TABLE II

| | | Elemental Analysis | | |
|---|---|---|---|---|
| Example | Emp. Formula | % Calcd. (Found) | | |
| | | C | H | N |
| 1 | $C_9H_{20}NO_2PS_2$ | 40.10(39.21) | 7.50(7.54) | 5.20(4.66) |
| 2 | NA | | | |
| 3 | $C_{10}H_{19}F_3NO_2PS_2$ | 35.59(36.30) | 5.68(5.40) | 4.15(4.13) |
| 4 | $C_6H_{14}NOPS_2$ | 34.10(33.99) | 6.68(6.23) | 6.63(6.29) |
| 5 | NA | | | |
| 6 | NA | | | |
| 7 | $C_8H_{18}NO_2PS_2$ | 37.60(38.10) | 7.10(7.05) | 5.48(5.49) |
| 8 | $C_6H_{14}NO_2PS_2$ | 31.71(31.41) | 6.21(6.43) | 6.16(6.16) |
| 9 | $C_7H_{16}NO_2PS_2$ | 34.83(35.13) | 6.68(6.68) | 5.80(5.56) |
| 10 | NA | | | |
| 11 | $C_7H_{16}NO_2PS_2$ | 34.83(34.39) | 6.68(6.34) | 5.80(6.12) |
| 12 | $C_7H_{16}NO_2PS_2$ | 34.84(34.97) | 6.68(6.80) | 5.80(5.65) |
| 13 | $C_8H_{18}NO_2PS_2$ | 37.62(36.81) | 7.10(7.02) | 5.48(6.19) |
| 14 | $C_9H_{20}NO_2PS_2$ | 40.13(41.04) | 7.48(7.64) | 5.20(5.09) |
| 15 | NA | | | |
| 16 | $C_9H_{20}NOPS_3$ | 37.87(39.58) | 7.06(7.38) | 4.91(4.99) |
| 17 | NA | | | |
| 18 | $C_9H_{20}NOPS_4$ | 34.00(35.74) | 6.34(6.65) | 4.41(3.78) |
| 19 | NA | | | |
| 20 | NA | | | |
| 21 | $C_6H_{14}NOPS_3$ | 29.61(30.48) | 5.80(5.76) | 5.76(5.88) |
| 22 | $C_7H_{16}NOPS_3$ | 32.66(33.61) | 6.27(7.06) | 5.44(6.57) |
| 23 | $C_7H_{16}NOPS_3$ | 32.66(32.48) | 6.27(6.09) | 5.44(5.28) |
| 24 | $C_7H_{16}NOPS_3$ | 32.66(33.14) | 6.26(6.42) | 5.44(5.65) |
| 25 | $C_8H_{18}NOPS_3$ | 35.40(36.16) | 6.68(6.93) | 5.16(5.36) |

TABLE II-continued

Elemental Analysis

| Example | Emp. Formula | % Calcd. (Found) C | H | N |
|---|---|---|---|---|
| 26 | C$_{10}$H$_{20}$NOPS$_3$ | 40.37(40.46) | 6.77(7.24) | 4.70(5.12) |
| 27 | C$_8$H$_{18}$NOPS$_3$ | 35.40(35.75) | 6.68(6.85) | 5.16(5.35) |
| 28 | C$_9$H$_{20}$NOPS$_3$ | 37.87(38.73) | 7.06(7.17) | 4.91(5.26) |
| 29 | C$_8$H$_{18}$NO$_2$PS$_2$ | 37.62(36.06) | 7.10(7.09) | 5.48(5.58) |
| 30 | C$_{10}$H$_{22}$NO$_2$PS$_2$ | 42.30(42.20) | 7.82(7.91) | 4.94(4.88) |
| 31 | C$_{11}$H$_{24}$NO$_2$PS$_2$ | 44.40(44.20) | 8.13(8.16) | 4.70(4.72) |
| 32 | C$_{14}$H$_{22}$NO$_2$PS$_2$ | 50.73(49.74) | 6.69(6.73) | 4.22(4.29) |
| 33 | C$_9$H$_{20}$NO$_2$PS$_3$ | 35.85(35.85) | 6.68(6.53) | 4.64(4.77) |
| 34 | C$_6$H$_{14}$NO$_2$PS$_2$ | 31.70(31.14) | 6.21(6.95) | 6.16(6.35) |
| 35 | C$_7$H$_{16}$NO$_2$PS$_2$ | 34.83(34.24) | 6.68(6.71) | 5.80(5.78) |
| 36 | C$_7$H$_{16}$NO$_2$PS$_2$ | 34.84(34.38) | 6.68(6.88) | 5.80(5.91) |
| 37 | C$_{10}$H$_{20}$NO$_2$PS$_2$ | 42.68(41.74) | 7.16(7.22) | 4.97(5.12) |
| 38 | C$_9$H$_{20}$NO$_2$PS$_2$ | 40.13(39.96) | 7.48(7.65) | 5.20(5.35) |
| 39 | C$_{10}$H$_{22}$NO$_2$PS$_2$ | 42.65(42.28) | 8.29(7.94) | 5.24(5.29) |
| 40 | C$_{10}$H$_{20}$NO$_2$PS$_2$ | 42.68(42.71) | 7.16(7.31) | 4.97(5.15) |
| 41 | C$_{10}$H$_{18}$NO$_2$PS$_3$ | 42.99(42.41) | 6.49(6.23) | 5.01(5.34) |
| 42 | C$_9$H$_{20}$NO$_2$PS$_3$ | 35.85(35.98) | 6.68(6.55) | 4.64(4.76) |
| 43 | NA | | | |
| 44 | C$_{11}$H$_{24}$NO$_2$PS$_2$ | 44.41(44.07) | 8.13(8.12) | 4.70(4.79) |
| 45 | C$_7$H$_{16}$NO$_2$PS$_2$ | 34.8(35.16) | 6.70(6.83) | 5.80(4.87) |
| 46 | C$_9$H$_{17}$N$_2$O$_2$PS$_2$ | 38.55(38.07) | 6.11(6.16) | 9.99(9.61) |
| 47 | | | | |
| 48 | | | | |
| 49 | C$_8$H$_{18}$NO$_2$PS$_2$ | 37.62(37.64) | 7.10(6.99) | 5.48(5.36) |
| 50 | C$_8$H$_{18}$NO$_2$PS$_2$ | 37.62(37.53) | 7.10(6.99) | 5.48(5.56) |
| 51 | C$_9$H$_{20}$NO$_2$PS$_2$ | 40.12(39.88) | 7.48(7.54) | 5.20(5.28) |
| 52 | C$_9$H$_{20}$NO$_2$PS$_2$ | 40.12(40.32) | 7.48(7.58) | 5.20(5.42) |
| 53 | C$_8$H$_{16}$NO$_2$PS$_2$ | 37.92(38.42) | 6.36(6.55) | 5.52(5.67) |
| 54 | C$_8$H$_{16}$NO$_2$PS$_2$ | 37.92(38.42) | 6.36(6.55) | 5.52(5.67) |
| 55 | C$_7$H$_{16}$NO$_3$PS$_2$ | 32.67(31.96) | 6.26(6.19) | 5.44(4.99) |
| 56 | NA | | | |
| 57 | NA | | | |
| 58 | NA | | | |
| 59 | NA | | | |
| 60 | NA | | | |
| 61 | NA | | | |
| 62 | NA | | | |
| 63 | C$_8$H$_{17}$FNO$_2$PS$_2$ | 35.15(35.67) | 6.27(5.98) | 5.12(4.69) |
| 64 | C$_9$H$_{20}$NO$_3$PS$_2$ | 37.88(37.73) | 7.06(7.16) | 4.91(4.73) |
| 65 | C$_9$H$_{16}$F$_4$NO$_2$PS$_2$ | 31.67(32.18) | 4.73(4.70) | 4.10(3.29) |
| 66 | C$_{13}$H$_{17}$F$_3$NOPS$_3$ | 40.29(41.98) | 4.42(5.24) | 3.62(3.72) |
| 67 | C$_9$H$_{20}$NOPS$_4$ | 34.40(35.74) | 6.34(6.65) | 4.41(3.55) |
| 68 | C$_8$H$_{18}$NOPS$_3$ | 35.40(35.49) | 6.68(6.54) | 5.16(5.02) |
| 69 | C$_8$H$_{18}$NOPS$_3$ | 35.40(35.96) | 6.68(6.70) | 5.16(5.21) |
| 70 | C$_9$H$_{20}$NOPS$_3$ | 37.86(39.03) | 7.06(7.48) | 4.90(4.94) |
| 71 | C$_9$H$_{22}$NOPS$_3$ | 37.86(38.84) | 7.06(7.42) | 4.90(5.13) |
| 72 | C$_9$H$_{20}$NOPS$_3$ | 37.86(39.48) | 7.06(7.42) | 4.90(4.80) |
| 73 | C$_9$H$_{20}$NOPS$_3$ | 37.86(39.26) | 7.06(7.62) | 4.9(4.95) |
| 74 | C$_8$H$_{16}$NOPS$_3$ | 35.66(37.50) | 5.98(6.57) | 5.19(6.57) |
| 75 | C$_7$H$_{16}$NO$_1$PS$_3$ | 30.75(31.79) | 5.90(6.20) | 5.12(4.65) |
| 76 | NA | | | |
| 77 | NA | | | |
| 78 | NA | | | |
| 79 | C$_{10}$H$_{19}$NO$_3$PS$_3$ | 36.45(37.01) | 6.11(6.31) | 4.25(4.57) |
| 80 | C$_{14}$H$_{22}$NOPS$_3$ | 48.38(50.57) | 6.38(6.44) | 4.03(3.82) |
| 81 | C$_{14}$H$_{21}$FNOPS$_3$ | 46.0(45.73) | 5.79(5.67) | 3.83(3.70) |
| 82 | C$_{15}$H$_{24}$NO$_2$PS$_3$ | 47.71(47.97) | 6.40(6.65) | 3.71(3.69) |
| 83 | C$_{15}$H$_{21}$F$_3$NOPS$_3$ | 43.35(44.76) | 5.09(5.12) | 3.37(3.13) |
| 84 | C$_{10}$H$_{21}$CLNOPS$_3$ | 35.96(36.60) | 6.34(6.60) | 4.19(3.74) |
| 85 | C$_{14}$H$_{21}$CLNOPS$_4$ | 40.6(43.04) | 5.10(5.20) | 3.38(2.82) |
| 86 | C$_{10}$H$_{19}$BrNOPS$_3$ | 31.91(32.67) | 5.08(5.34) | 3.72(3.33) |
| 87 | C$_{16}$H$_{24}$NOPS$_3$ | 51.4(51.18) | 6.47(6.60) | 3.75(3.99) |
| 88 | C$_{11}$H$_{22}$NO$_3$PS$_3$ | 38.46(38.85) | 6.45(6.68) | 4.07(4.22) |
| 89 | C$_{11}$H$_{24}$NO$_2$PS$_3$ | 40.09(38.79) | 7.34(6.71) | 4.25(4.11) |
| 90 | NA | | | |
| 91 | NA | | | |
| 92 | NA | | | |
| 93 | NA | | | |
| 94 | | | | |
| 95 | C$_{10}$H$_{18}$NO$_2$PS$_2$ | 42.99(40.58) | 6.49(6.86) | 5.01(4.81) |
| 96 | C$_8$H$_{15}$F$_3$NO$_2$PS$_2$ | 31.06(31.69) | 4.89(4.80) | 4.52(4.60) |
| 97 | C$_7$H$_{14}$NO$_2$PS$_2$ | 35.13(35.10) | 5.89(6.03) | 5.85(5.97) |
| 98 | C$_8$H$_{18}$NO$_2$PS$_2$ | 37.62(37.80) | 7.10(7.12) | 5.48(5.72) |
| 99 | C$_9$H$_{20}$NO$_2$PS$_2$ | 40.10(39.58) | 7.48(7.55) | 5.20(5.01) |
| 100 | C$_9$H$_{20}$NO$_2$PS$_2$ | 40.10(39.60) | 7.48(7.67) | 5.20(5.18) |
| 101 | C$_9$H$_{20}$NO$_2$PS$_2$ | 40.10(38.83) | 7.48(7.48) | 5.20(4.87) |
| 102 | NA | | | |
| 103 | NA | | | |
| 104 | C$_{14}$H$_{21}$FNO$_2$PS$_2$ | 48.11(48.01) | 6.05(6.10) | 4.00(4.04) |
| 105 | C$_{15}$H$_{24}$NO$_3$PS$_2$ | 49.84(49.59) | 6.69(6.44) | 3.87(4.23) |
| 106 | C$_{15}$H$_{21}$F$_3$NO$_2$PS$_2$ | 45.10(45.18) | 5.30(5.48) | 3.50(3.44) |
| 107 | NA | | | |
| 108 | C$_{11}$H$_{22}$NO$_2$PS$_2$ | 44.72(44.52) | 7.50(7.65) | 4.74(4.90) |
| 109 | C$_9$H$_{18}$NO$_2$PS$_2$ | 40.4(37.86) | 6.78(6.91) | 5.23(6.13) |
| 110 | C$_9$H$_{16}$NO$_2$PS$_2$ | 40.73(40.49) | 6.07(6.32) | 5.27(5.35) |
| 111 | C$_{18}$H$_{24}$NO$_2$PS$_2$ | 56.66(55.68) | 6.34(6.49) | 3.67(3.42) |
| 112 | C$_{14}$H$_{21}$BrNO$_2$PS$_2$ | 40.97(41.43) | 5.15(5.12) | 3.41(3.42) |
| 113 | C$_{14}$H$_{20}$ClFNO$_2$PS$_2$ | 43.80(44.35) | 5.25(4.68) | 3.64(2.33) |
| 114 | C$_9$H$_{20}$NO$_2$PS$_2$ | 40.12(40.45) | 7.48(6.74) | 5.20(4.16) |
| 115 | C$_{10}$H$_{22}$NO$_2$PS$_2$ | 42.37(41.58) | 7.82(7.66) | 4.94(4.82) |
| 116 | C$_{15}$H$_{23}$N$_2$O$_5$PS$_2$ | 48.11(47.80) | 6.19(6.52) | 7.48(7.33) |
| 117 | C$_{14}$H$_{17}$F$_5$NO$_2$PS$_2$ | 39.90(40.14) | 4.06(4.16) | 3.32(3.60) |
| 118 | C$_{14}$H$_{20}$Cl$_2$NO$_2$PS$_2$ | 42.00(41.93) | 5.03(4.88) | 3.49(2.77) |
| 119 | NA | | | |
| 120 | NA | | | |
| 121 | C$_{10}$H$_{20}$NO$_4$PS$_2$ | 38.32(38.48) | 6.43(6.60) | 4.47(4.88) |
| 122 | C$_{14}$H$_{22}$NO$_2$PS$_2$ | 50.73(52.49) | 6.69(6.86) | 4.22(3.95) |
| 123 | C$_{14}$H$_{21}$FNO$_2$PS$_2$ | 48.11(46.97) | 6.00(6.02) | 4.00(3.76) |
| 124 | C$_{15}$H$_{24}$NO$_3$PS$_2$ | 49.84(49.17) | 6.69(6.71) | 3.87(3.72) |
| 125 | C$_{15}$H$_{21}$F$_3$NO$_2$PS$_2$ | 45.10(45.60) | 5.30(5.45) | 3.50(3.72) |
| 126 | C$_{10}$H$_{21}$ClNO$_2$PS$_2$ | 37.78(36.90) | 6.66(6.74) | 4.40(4.65) |
| 127 | C$_{14}$H$_{21}$ClNO$_2$PS$_2$ | 42.25(42.01) | 5.31(5.49) | 3.52(3.80) |
| 128 | C$_{10}$H$_{19}$BrNO$_2$PS$_2$ | 33.30(33.93) | 5.31(5.41) | 22.18(20.64) |
| 129 | C$_{16}$H$_{24}$NO$_2$PS$_2$ | 53.75(53.71) | 6.70(6.72) | 3.91(3.96) |
| 130 | C$_{11}$H$_{22}$NO$_4$PS$_2$ | 40.35(40.31) | 6.77(6.87) | 4.27(4.67) |
| 131 | C$_{14}$H$_{21}$N$_2$O$_4$PS$_2$ | 44.60(43.52) | 5.62(5.74) | 7.44(7.21) |
| 132 | C$_{15}$H$_{21}$N$_2$O$_2$PS$_2$ | 50.50(50.59) | 5.93(6.08) | 7.86(7.74) |
| 133 | C$_{15}$H$_{22}$NO$_3$PS$_2$ | 50.10(47.67) | 6.17(6.49) | 3.89(4.11) |
| 134 | C$_{14}$H$_{21}$BrNO$_2$PS$_2$ | 40.97(40.86) | 5.15(5.01) | 3.41(2.98) |
| 135 | C$_{14}$H$_{21}$ClNO$_3$PS$_2$ | 44.02(43.64) | 5.54(5.55) | 3.66(3.60) |
| 136 | C$_{18}$H$_{24}$NO$_2$PS$_2$ | 56.60(55.96) | 6.34(6.13) | 3.67(3.47) |
| 137 | C$_{11}$H$_{22}$NO$_2$PS$_2$ | 44.72(44.25) | 7.50(7.71) | 4.74(4.62) |
| 138 | C$_{14}$H$_{20}$ClFNO$_2$PS$_2$ | 43.80(43.63) | 5.25(5.29) | 3.64(3.47) |
| 139 | C$_{14}$H$_{17}$F$_5$NO$_2$PS$_2$ | 39.90(39.99) | 4.06(4.13) | 3.32(3.45) |
| 140 | C$_{10}$H$_{22}$NO$_2$PS$_2$ | 42.37(42.10) | 7.82(7.58) | 4.94(5.30) |
| 141 | C$_{13}$H$_{20}$NO$_2$PS$_2$ | 49.18(49.13) | 6.35(6.34) | 4.41(4.79) |
| 142 | C$_{10}$H$_{20}$NO$_4$PS$_2$ | 38.30(38.21) | 6.43(6.53) | 4.46(4.76) |
| 143 | C$_9$H$_{19}$ClNO$_2$PS$_2$ | 35.57(35.34) | 6.30(6.36) | 4.61(4.81) |
| 144 | C$_{21}$H$_{28}$NO$_3$PS$_2$ | 57.64(55.83) | 6.44(6.43) | 3.20(3.49) |
| 145 | C$_{15}$H$_{21}$ClNO$_4$PS$_2$ | 43.95(43.74) | 5.16(5.22) | 3.41(3.48) |
| 146 | C$_{11}$H$_{22}$NO$_2$PS$_2$ | 44.72(44.55) | 7.50(7.46) | 4.74(4.62) |
| 147 | C$_9$H$_{20}$NO$_3$PS$_2$ | 37.8(38.09) | 7.10(7.36) | 4.6(5.45) |
| 148 | C$_{14}$H$_{22}$NO$_3$PS | 53.3(54.74) | 7.00(7.23) | 4.4(5.20) |
| 149 | C$_9$H$_{17}$N$_2$O$_3$PS | 40.89(41.03) | 6.48(6.74) | 10.60(10.05) |
| 150 | C$_9$H$_{20}$NO$_4$PS | 40.10(40.71) | 7.48(8.00) | 5.20(4.68) |
| 151 | C$_{10}$H$_{21}$ClNO$_3$PS | 39.79(38.14) | 7.00(7.00) | 4.64(4.58) |
| 152 | C$_{14}$H$_{21}$FNO$_3$PS | 50.43(50.64) | 6.35(6.44) | 4.20(4.21) |
| 153 | C$_{15}$H$_{24}$NO$_4$PS | 52.15(51.79) | 7.00(7.04) | 4.05(4.38) |
| 154 | C$_{15}$H$_{21}$F$_3$NO$_3$PS | 46.99(47.57) | 5.52(5.69) | 3.65(3.60) |
| 155 | C$_{14}$H$_{21}$ClNO$_3$PS$_2$ | 44.00(43.80) | 5.54(572) | 3.66(3.81) |
| 156 | C$_{16}$H$_{24}$NO$_3$PS | 56.28(55.80) | 7.08(7.08) | 4.10(3.92) |
| 157 | C$_{14}$H$_{22}$NO$_3$PS | 48.39(48.54) | 6.38(6.57) | 4.03(4.11) |
| 158 | C$_{15}$H$_{24}$NO$_3$PS | 54.69(54.01) | 7.34(7.56) | 4.25(4.29) |
| 159 | C$_{14}$H$_{21}$N$_2$O$_5$PS | 46.65(46.33) | 5.83(6.11) | 7.77(7.56) |
| 160 | C$_9$H$_{19}$ClNO$_3$PS | 37.56(36.96) | 6.65(6.80) | 4.86(4.75) |
| 161 | C$_{15}$H$_{22}$NO$_4$PS | 52.46(51.71) | 6.45(6.83) | 4.07(4.29) |
| 162 | C$_{18}$H$_{24}$NO$_3$PS | 59.15(59.26) | 6.61(6.79) | 3.83(3L85) |
| 163 | C$_{14}$H$_{21}$BrNO$_3$PS | 42.64(42.89) | 5.36(5.48) | 3.55(3.44) |
| 164 | C$_{14}$H$_{20}$ClFNO$_3$PS | 45.71(45.60) | 5.48(5.66) | 3.80(3.91) |
| 165 | C$_{14}$H$_{17}$F$_5$NO$_3$PA | 41.48(41.54) | 4.22(3.95) | 3.45(3.66) |
| 166 | C$_{14}$H$_{10}$Cl$_2$NO$_3$PS | 43.75(43.47) | 5.24(5.31) | 3.64(3.88) |
| 167 | C$_{13}$H$_{20}$NO$_3$PS | 51.8(52.25) | 6.69(6.59) | 4.64(4.76) |
| 168 | C$_{13}$H$_{19}$FNO$_3$PS | 48.89(48.56) | 5.99(6.05) | 4.38(4.66) |
| 169 | C$_{13}$H$_{18}$ClFNO$_3$PS | 44.10(43.84) | 5.12(5.32) | 3.95(4.03) |
| 170 | C$_{14}$H$_{21}$FNO$_3$PS | 50.44(49.90) | 6.35(6.61) | 4.20(4.83) |
| 171 | C$_{14}$H$_{20}$FN$_2$O$_5$PS | 50.78(49.03) | 5.33(5.31) | 7.40(7.34) |
| 172 | C$_{14}$H$_{19}$F$_3$NO$_3$PS | 45.52(45.52) | 5.18(5.11) | 3.79(3.84) |
| 173 | C$_{18}$H$_{18}$NO$_2$PS | 19.64(50.10) | 6.94(6.80) | 3.21(3.45) |
| 174 | C$_{16}$H$_{24}$NO$_4$PS | 53.76(52.53) | 6.76(6.56) | 3.91(3.82) |
| 175 | C$_{15}$H$_{24}$NO$_3$PS | 54.69(54.68) | 7.34(7.29) | 4.25(4.16) |
| 176 | C$_{15}$H$_{23}$N$_2$O$_5$PS | 48.11(47.80) | 6.19(6.52) | 7.48(7.33) |
| 177 | NA | | | |
| 178 | C$_{14}$H$_{20}$Cl$_2$NO$_3$PS | 43.75(43.74) | 5.24(5.27) | 3.64(3.56) |
| 179 | NA | | | |
| 180 | C$_{15}$H$_{21}$N$_2$O$_3$PS | 52.92(52.20) | 6.21(6.54) | 8.23(8.11) |

TABLE III

Nuclear Magnetic Resonance Data (ppm, δ)

Example 1: 8.90(s, 1H, CCH); 4.30(m, 2H, OCH₂CH₃); 3.68(m, 1H, SCH) 3.60(m, 2H, NCH₂); 1.64(m, 2H, SCHCH₂); 1.40(m, 3H, SCH(CH₃); 1.40 (t, 3H, OCH₂CH₃); 1.40(t, 3H, NCH₂CH₃); 1.20(m, 3H, SCH(CH₃)CH₂CH₃)

Example 2: 4.20(m, 2H, OCH₂); 3.80(m, 2H, NCH₂), 3.40(m, 1H, SCH), 2.20(s, 3H, NCOCH₃); 1.64(m, 2H, SCHCH₂); 1.40(t, 3H, OCH₂CH₃); 1.40 (t, 3H, NCH₂CH₃); 1.40(m, 3H, SCHCH₃); 1.00(m, 3H, SCH(CH₃)CH₂CH₃)

Example 3: 4.30(m, 2H, OCH₂); 3.80(m, 2H, NCH₂), 3.40(m, 1H, SCH); 1.64(m, 2H, SCHCH₂); 1.40(t, 3H, OCH₂CH₃); 1.40(t, 3H, NCH₂CH₃); 1.40 (3H, SCHCH₃); 1.00(m, 3H, SCH(CH₃)CH₂CH₃)

Example 4: 8.88(s, 1H, OCH); 4.38(m, 2H, OCH₂); 3.70(m, 2H, NCH₂); 2.41(d, 3H, SCH₃); 1.40(q, 6H, NCH₂CH₃ and OCH₂CH₃)

Example 5: 8.90(s, 1H, OCH); 4.38(m, 2H, OCH₂); 4.30(d, 2H, SCH₂); 3.58(m, 2H, NCH₂); 2.58(s, 3H, ring CH₃); 1.38(m, 6H, NCH₂CH₃ and OCH₂CH₃)

Example 6: 8.75(s, 1H, OCH); 4.40(m, 4H, OCH₂ and NCH₂); 3.58(m, 1H, SCH); 1.84(m, 2H, SCHCH₂); 1.50(m, D6H, OCH₂CH₃ and SCHCH₃); 1.10(m, 3H, SCH(CH₃)CH₂CH₃)

Example 7: 8.90(s, 1H, OCH); 4.30(m, 2H, OCH₂); 3.48(m, 1H, SCH); 308(d, 3H, NCH₃)D; 1.78(m, 2H, SCHCH₂); 1.38(t, 6H, OCH₂CH₃ and SCHCH₃); 1.08(m, 3H, SCH(CH₃)CH₂CH₃)

Example 8: 8.92(s, 1H, OCH); 4.38(m, 2H, OCH₂); 3.15(m, 2H, SCH₂) 3.08(d, 3H, NCH₃); 1.38(dt, 6H, SCH₂CH₃ and OCH₂CH₃)

Example 9: 8.90(s, 1H, OCH); 3.80(d, 3H, OCH₃); 3.40(m, 1H, SCH), 3.00(d, 3H, NCH₃); 1.70(m, 2H, SCHCH₂); 1.40(t, 6H, OCH₂CH₃ and SCHCH₃); 1.00(m, 3H, SCH(CH₃)CH₂CH₃)

Example 10: 8.85(s, 1H, OCH); 7.50(s, 4H, aromatic); 3.50(m, 1H, SCH); 3.19(d, 3H, NCH₃); 1.70(m, 2H, SCHCH₂); 1.38(d, 3H, SCHCH₃); 0.98 (m, 3H, SCH(CH₃)CH₂CH₃)

Example 11: 8.90(s, 1H, OCH); 4.30(m, 2H, OCH₂); 3.00(d, 3H, NCH₃); 2.80(m, 2H, SCH₂); 1.78(m, 2H, SCH₂CH₂); 1.40(t, 3H, OCH₂CH₃); 1.00 (t, 3H, SCH₂CH₂CH₃)

Example 12: 8.88(s, 1H, OCH); 4.25(m, 2H, OCH₂); 3.50(m, 1H, SCH), 3.02(d, 3H, NCH₃); 1.20(m, 9H, OCH₂CH₃ and SCH(CH₃)₂

Example 13: 8.90(s, 1H, OCH); 4.20(m, 2H, OCH₂); 2.98(d, 3H, NCH₃); 1.58(d, 9H. SCH(CH₃)₃; 1.30(t, 3H, OCH₂CH₃)

Example 14: 8.90(s, 1H, OCH); 4.30(m, 2H, OCH₂); 3.42(m, 1H, SCH); 1.78(m, 4H, SCH(CH₂CH₃)₂; 1.50(t, 3H, OCH₂CH₃); 1.10(m, 6H, SCH (CH₂CH₃)₂

Example 15: 8.95(s, 1H, OCH); 5.90(m, 1H, SCH₂CH=CH₂); 5.36(m, 2H, SCH₂CH=CH₂); 4.30(m, 2H, OCH₂); 3.60(m, 2H, SCH₂CH=CH₂); 3.00(d, 3H NCH₃); 1.40(t, 3H, OCH₂CH₃)

Example 16: 9.33(d, 1H, CHS); 4.24(m, 4H, OCH₂ and NCH₂); 3.40(m, 1H, SCH); 1.80(m, 2H, SCHCH₂); 1.42(m, 9H, OCH₂CH₃, SCHCH₃ and NCH₂CH₃); 1.18(m, 3H, SCHOCH₃)CH₂CH₃

Example 17: 9.35(d, 1H, CHS); 5.30(dd, 2H, NCH₂SCH₃); 4.38(m, 2H, OCH₂); 3.40(m, 1H, SCH); 2.20(s, 3H, SCH₃); 1.75(m, 2H, SCHCH₂); 1.40(m, 6H, OCH₂CH₃ and SCHCH₃); 1.10(m, 3H, SCH(CH₃)CH₂CH₃)

Example 18: 9.35 (d, 1H, CHS); 4.30(m, 4H, OCH₂ and NCH₂); 2.40(d, 3H, SCH₃); 1.40(m, 6H, OCH₂CH₃ and NCH₂CH₃)

Example 19: 9.30(d, 1H, CHS); 4.40(m, 2H, OCH₂); 3.50(d, 3H, NCH₃); 3.00(m, 2H, SCH₂); 1.80(m, 2H, SCH₂CH₂); 1.50(t, 3H, OCH₂CH₃) 1.04 (m, 3H, SCH₂CH₂CH₃)

Example 20: 9.30(d, 1H, CHS); 4.38(m, 2H, OCH₂); 3.60(m, 1H, SCH), 3.35(d, 3H, NCH₃); 1.42(t, 9H, OCH₂CH₃ and SCH(CH₃)₂

Example 21: 9.35(bd, 1H, CHS); 4.22(m, 2H, OCH₂); 3.38(m, 1H, SCH); 1.70(m, 2H, SCHCH₂); 1.38(m, 6H, OCH₂CH₃ and SCHCH₃); 1.00(m, 3H, SCH(CH₃)CH₂CH₃

Example 22: 9.30(d, 1H, CHS); 4.20(m, 2H, OCH₂); 3.40(d, 3H, OCH₃); 3.38(m, 1H, SCH); 1.80(m, 2H, SCHCH₂); 1.45(m, 6H, OCH₂CH₃ and SCHCH₃); 1.00(m, 3H, SCH(CH₃)CH₂CH₃)

Example 23: 9.35(d, 1H, CHS); 6.00(m, 1H, NCH₂CH=CH₂); 5.40(m, 2H, NCH₂CH=CH₂); 4.38(m, 4H, DNCH₂ and OCH₂); 3.38(m, 1H, SCH); 1.80(m, 2H, SCHCH₂); 1.50(m, 6H, OCH₂CH₃ and SCHCH₃); 1.05(m, 3H, SCH(CH₃)CH₂CH₃)

Example 24: 9.30(d, 1H, CHS); 4.36(m, 2H, OCH₂); 3.42(d, 3H, NCH₃); 1.58(d, 9H, SC(CH₃)₃; 1.42(t, 3H, OCH₂CH₃)

TABLE III (cont.)

Nuclear Magnetic Resonance Data (ppm, δ)

Example 25: 9.35(d, 1H, CHS); 4.36(m, 2H, OCH₂); 3.38(d, 3H, NCH₃); 3.28(m, 1H, SCH); 1.78(m, 4H, SCH(CH₂CH₃)₂; 1.40(t, 3H, OCH₂CH₃); 1.00(m, 6H, SCH(CH₂CH₃)₂

Example 26: 9.30(d, 1H, CHS); 4.40(m, 2H, OCH₂); 3.40(d, 3H, NCH₃); 3.38(m, 1H, SCH); 1.78(m, 2H, SCHCH₂); 1.50(t, 6H, OCH₂CH₃) and SCHCH₃); 1.05(m, 3H, SCH(CH₃)CH₂CH₃)

Example 27: 9.35(d, 1H, CHS); 4.35(m, 2H, OCH₂); 3.90(m, 2H, NCH₂); 3.38(m, 1H, SCH); 1.78(m, 4H, SCHCH₂ and NCH₂CH₂); 1.40(m, 6H, OCH₂CH₃ and SCHCH₃); 1.00(m, 6H, NCH₂CH₂CH₃ and SCH(CH₃)CH₂CH₃)

Example 28: Not Available

Example 29: 9.30(d, 1H, CHS); 7.10(m, 5H, aromatic); 5.00(m, 2H, NCH₂); 4.00(m, 2H, OCH₂); 3.38(m, 1H, SCH); 1.78(m, 2H, SCHCH₂): 1.50(t, 6H, OCH₂CH₃ and SCHCH₃); 1.00(m, 3H, SCH(CH₃)CH₂CH₃)

Example 30: 9.30(d, 1H, CHS); 5.10(d, 2H, NCH₂); 4.38(m, 2H, OCH₂); 3.40(m, 1H, SCH); 2.50(S, 3H, NCH₂SCH₃); 1.75(m, 2H, SCHCH₂); 100 (m, SCH(CH₃)—H₂CH₃)

Example 31: 9.35(d, 1H, CHS); 4.30(m, 2H, OCH₂); 3.36(d, 3H, NCH₃); 2.90(m, 2H, SCH₂); 1.38(dt, 6H, OCH₂CH₃ and SCH₂CH₃)

Example 32: 9.35(d, 1H. CHS); 4.35(m, 2H, OCH₂); 3.35(d, 3H, NCH₃); 3.00(m, 2H, SCH₂); 1.80(m, 2H, SCH₂CH₂); 1.50(t, 3H, OCH₂CH₃); 1.02(t, 3H, SCH₂CH₂CH₃)

Example 33: 9.30(d, 1H, CHS); 4.38(m, 2H, OCH₂); 3.50(m, 1H, CSCH); 3.36(d, 3H, NCH₃); 1.50(t, 9H, OCH₂CH₃ and SCH(CH₃)₂)

Example 34: 9.38(d, 1H, CHS); 6.10(m, 1H, NCH₂CH=CH₂); 5.48(m, 2H, NCH₂CH=CH₂); 4.78(m, 2H, SCH₂); 4.40(m, 2H, OCH₂); 3.40(m, 1H, SCH); 1.80(m, 2H, SCHCH₂); 1.40(m, 6H, OCH₂CH₃ and SCHCH₃); 1.00(m, 3H, SCH(CH₃)CH₂CH₃)

Example 35: 9.40(d, 1H, CHS); 4.35(m, 2H, OCH₂); 3.38(m, 1H, SCH); 3.30(d, 3H, NCH₃); 1.75(m, 4H, SCH(CH₂CH₃); 1.50(t, 3H, OCH₂CH₃); 1.10(m, 6H, SCH(CH₂CH₃)₂

Example 36: 9.30(d, 1H, CHS); 4.30(m, 4H, OCH₂ and NCH₂); 3.40(m, 1H, SCH); 1.80(m, 4H, SCH(CH₂CH₃)₂; 1.50(t, 3H, OCH₂CH₃); 1.08(m, 6H, SCH(CH₂CH₃)₂

Example 37: 8.90(S, 1H, OCH); 6.00(m, 1H, NCH₂CH=CH₂); 5.40(m, 2H, NCH₂CH=CH₂); 4.38(m, 4H, OCH₂, NCH₂); 3.42(m, 1H, SCH) 1.78(m, 2H, SCHCH₂); 1.50(m, 6H, OCH₂CH₃ and SCHCH₃); 1.02(m, 3H, SCH(CH₃)CH₂ CH₃)

Example 38: 8.85(S, 1H, CCH); 4.40(dd, 2H, NCH₂CHCH); 4.38(m, 2H, OCH₂); 3.40(m, 1H, SCH); 2.38(t, 1H, NCH₂CHCH); 1.80(m, 2H, SCHCH₂) 1.50(m, 6H, OCH₂CH₃ and SCHCH₃); 1.10(m, 3H, SCH(CH₃)CH₂CH₃)

TABLE III (cont.)-continued

Example 39: 8.9(S, 1H, CCH); 4.80(d, 2H, NCH$_2$); 3.30(m, 2H, OCH$_2$); 3.38(m, 1H, SCH) 2.30(S, 3H, NCH$_2$SCH$_3$); 1.78(m, 2H, SCHCH$_2$); 1.50 (m, 6H, OCH$_2$CH$_3$ and SCHCH$_3$); 1.02(m, 3H, SCH(CH$_3$)CH$_2$CH$_3$)

Example 44: 8.90(s, 1H, COH); 3.50(m, 3H, OCH$_2$, SCH); 3.00 (m, 2H, NCH$_2$); 1.78(m, 2H, SCHCH$_2$); 1,50(m, 10H, OCH$_2$CH$_3$, SCHCH$_3$ and NCH$_2$CH$_2$ CH$_2$CH$_3$); 1.00(m, 6H, SCH(CH$_3$)CH$_2$CH$_3$ and NCH$_2$CH$_2$CH$_2$CH$_3$).

Example 45: 8.70(d, 1H, COH); 8.65 (s, NHCHO); 4.20(m, 2H, OCH$_2$); 3.38(m, 1H, SCH); 1.78(m, 2H, SCHCH$_2$); 1.50(m, 6H, OCH$_2$CH$_3$ and SCHCH$_3$); 1.02(m, 3H, SCH(CH$_3$)CH$_2$CH$_3$).

Example 46: 8.70(s, 1H, COH); 4.68(d, 2H, NCH$_2$CN); 4.48(m, 2H, OCH$_2$); 3.42(m, 1H, SCH); 1.78(m, 2H, SCHCH$_2$); 1.50(m, 6H, OCH$_2$CH$_3$ and SCHCH$_3$); 1.02(m, 3H, SCH(CH$_3$)CH$_2$CH$_3$).

Example 49: 8.68(S, 1H, COH); 4.30(m, 2H, OCH$_2$); 3.10(d, 3H, NCH$_3$); 2.80(m, 2H, SCH$_2$); 1.98(m, 1H, SCH$_2$CH); 1.48(t, 3H, OCH$_2$CH$_3$): 1.00 (d, 6H, SCH$_2$CH(CH$_3$)$_2$).

Example 50: 8.70(s, 1H, COH); 4.40(m, 2H, OCH$_2$); 3.10(d, 3H, NCH$_3$); 3.00(m, 2H, SCH$_2$); 1.55(m, 7H, OCH$_2$CH$_3$ and SCH$_2$CH$_2$CH$_2$CH$_3$); 1.00(m, 3H, SCH$_2$CH$_2$CH$_2$CH$_3$).

Example 51: 8.70(s, 1H, COH); 4.38(m, 2H, OCH$_2$); 3.10(d, 3H, NCH$_3$); 3.05(m, 2H, SCH$_2$); 1.70(m, 6H, OCH$_2$CH$_3$ and SCH$_2$CH$_2$CH); 1.10(d, 6H, SCH$_2$ CH$_2$CH(CH$_3$)$_2$.

Example 52: 8.80(s, 1H, COH); 4.38(m, 2H, OCH$_2$); 3.10(d, 3H, NCH$_3$); 3.00(m, 2H, SCH$_2$); 1.70(m, 6H, OCH$_2$CH$_3$ and SCH$_2$CH(CH$_3$)CH$_2$CH$_3$); 1.00(m, 6H, SCH$_2$CH(CH$_3$)CH$_2$CH$_3$).

Example 53: 8.75(s, 1H, COH); 4.38(m, 2H, OCH$_2$); 3.30(m, 1H, SCH); 3.10 (d, 3H, NCH$_3$); 1.78(m, 2H, SCHCH$_2$); 1.50(m, 8H, OCH$_2$CH$_3$ and SCH(CH$_3$)CH$_2$ CH$_2$); 1.00(m, 3H, SCH(CH$_3$)CH$_2$CH$_2$CH$_3$).

Example 54: 8.70(s, 1H, COH); 590(m, 1H, SCH$_2$CH$_2$CH=CH$_2$); 5.20(m, 2H, SCH$_2$CH$_2$CH=CH$_2$); 4.38(m, 2H, OCH$_2$); 3.20(d, 3H, NCH$_3$); 3.10(m, 2H, SCH$_2$CH$_3$); 2.60(m, 2H, SCH$_2$); 1.50(t, 3H, OCH$_2$CH$_3$).

TABLE III (cont.)
Nuclear Magnetic Resonance Data (ppm, δ)

Example 55: 8.75(s, 1H, COH); 4.40(m, 2H, OCH$_2$); 3.70(m, 2H, SCH$_2$CH$_2$OCH$_3$); 3.40(s, 3H, SCH$_2$CH$_2$OCH$_3$), 3.20(d, 3H, NCH$_3$); 3.15(m, 2H, SCH$_2$); 1.50(t, 3H, OCH$_2$CH$_3$).

Example 56: 8.75(s, 1H, COH); 4.40(m, 2H, OCH$_2$); 3.60(m, 1H, SCH); 3.00 (d, 3H, NCH$_3$); 1.78(m, 2H, SCHCH$_2$); 1.50(m, 3H, SCHCH$_3$); 1.00(m, 3H, SCH(CH$_3$)CH$_2$CH$_3$).

Example 57: 8.80(s, 1H, COH); 4.40(m, 2H, OCH$_2$); 3.70(m, 3H, NCH$_2$ and SCH); 1.60(m, 7H, OCH$_2$CH$_3$ and SCH(CH$_2$CH$_3$)$_2$; 1.00(m, 6H, SCH(CH$_2$ CH$_3$)$_2$.

Example 58: 8.75(s, 1H, COH); 4.40(m, 2H, OCH$_2$); 3.60(m, 2H, NCH$_2$); 2.98(m, 2H, SCH$_2$); 1.80(m, 2H, SCH$_2$CH$_2$); 1.40(m, 6H, NCH$_2$CH$_3$ and OCH$_2$CH$_3$); 1.00(m, 3H, SCH$_2$CH$_2$CH$_3$)

Example 59: 8.75(d, 1H, COH); 8.70(s, 1H, NHCHO); 4.40(m, 2H, OCH$_2$); 3.00(m, 2H, SCH$_2$); 1.80(m, 2H, SCH$_2$CH$_2$); 1.50(m, 3H, OCH$_2$CH$_3$); 1.10 (m, 3H, SCH$_2$CH$_2$CH$_3$)

Example 60: 8.70(s, 1H, COH); 4.20(m, 2H, OCH$_2$); 3.65(m, 2H, NCH$_2$); 4.40(m, 1H, SCH); 1.78(m, 4H, OCH$_2$CH$_2$ and SCH(CH$_3$)CH$_2$); 1.40(m, 6H, NCH$_2$CH$_3$ and SCH(CH$_3$)); 1.00(m, 6H, OCH$_2$CH$_2$CH$_3$ and SCH(CH$_3$)CH$_2$CH$_3$)

Example 61: 8.70(s, 1H, COH); 4.30(m, 2H, OCH$_2$); 3.50(m, 1H, SCH); 3.20(d, 3H, NCH$_3$); 1.80(m, 4H, OCH$_2$CH$_2$ and SCH(CH$_3$)CH$_2$); 1.50(m, 3H, SCH(CH$_3$)CH$_2$CH$_3$); 1.00(m, 6H, OCH$_2$CH$_2$CH$_3$ and SCH(CH$_3$)CH$_2$CH$_3$)

Example 62: 8.80(s, 1H, COH); 4.80(m, 2H, OCH$_2$); 3.95(m, 2H, NCH$_2$); 3.58(m, 1H, SCH); 1.90(m, 2H, SCH(CH$_3$)CH$_2$); 1.62(m, 6H, NCH$_2$CH$_3$ and SCH(CH$_3$)CH$_2$CH$_3$); 1.20(m, 3H, SCH(CH$_3$)CH$_2$CH$_3$)

Example 63: 8.70(s, 1H, COH); 5.10(m, 2H, OCH$_2$CH$_2$F); 4.80(m, 2H,OCH$_2$CH$_2$F); 3.60(m, 1H, SCH); 3.10(d, 3H, NCH$_3$); 1.78(m, 2H, SCH(CH$_3$)CH$_2$); 1.60(m, 3H, SCH(CH$_3$)); 1.10(m, 3H, SCH(CH$_3$)CH$_2$CH$_3$)

Example 64: 8.80(s, 1H, COH); 4.38(m, 2H, OCH$_2$CH$_2$OCH$_3$); 3.90(m, 2H, OCH$_2$CH$_2$OCH$_3$); 3.60(s, 3H, OCH$_2$CH$_2$OCH$_3$); 3.30(d, 3H, NCH$_3$); 1.78(m, 2H, SCH(CH$_3$)CH$_2$CH$_3$); 1.50(m, 3H, SCH(CH$_3$)CH$_2$CH$_3$); 1.10(m, 3H, SCH(CH$_3$)CH$_2$ CH$_3$)

Example 65: 8.75(s, 1H, COH); 7.00, 6.10 and 5.20(m, 1H, OCH$_2$CF$_2$CF$_2$H); 4.60(m, 2H, OCH$_2$); 3.60(m, 1H, SCH); 3.20(d, 3H, NCH$_3$); 1.80(m, 2H, SCH(CH$_3$)CH$_2$CH$_3$); 1.50(m, 3H, SCH(CH$_3$)CH$_2$CH$_3$); 1.10(m, 3H, SCH(CH$_3$)CH$_2$CH$_3$)

Example 66: 9.30(d, 1H, CHS); 7.60(s, 4H, OC$_6$H$_4$—3CF$_3$); 3.50(d, 3H, NCH$_3$) 3.40(m, 1H, SCH); 1.78(m, 2H, SCH(CH$_3$)CH$_2$CH$_3$); 1.50(m, 3H, SCH(CH$_3$)) 1.00 (m, 3H, SCH(CH$_3$)CH$_2$CH$_3$)

Example 67: 9.35(d, 1H, CHS); 5.30(dd, 2H, NCH$_2$SCH$_3$); 4.40(m, 2H, OCH$_2$); 3.50(m, 1H, SCH); 2.40(s, 3H, NCH$_2$SCH$_3$); 1.78(m, 2H, SCH(CH$_3$)CH$_2$); 1.60 (m, 6H, OCH$_2$CH$_3$ and SCH(CH$_3$)CH$_2$CH$_3$); 1.00(m, 3H, SCH(CH$_3$)CH$_2$CH$_3$)

Example 68: 9.30(d, 1H, CHS); 4.40(m, 2H, OCH$_2$); 3.50(d, 3H, NCH$_3$); 2.90 (dd, 2H, SCH$_2$); 2.00(m, 1H, SCH$_2$CH); 1.50(t, 3H, OCH$_2$CH$_3$); 1.00(d, 6H, SCH$_2$CH(CH$_3$)$_2$)

Example 69: 9.35(d, 1H, CHS); 4.40(m, 2H, OCH$_2$); 3.50(d, 3H, NCH$_3$); 3.00(m, 2H, SCH$_2$); 1.80(m, 2H, SCH$_2$CH$_2$); 1.58(m, 5H, SCH$_2$CH$_2$CH$_2$ and OCH$_2$CH$_3$); 1.00(m, 3H, SCH$_2$CH$_2$CH$_2$CH$_3$)

Example 70: 9.35(d, 1H, CHS); 4.40(m, 2H, OCH$_2$); 3.50(d, 3H, NCH$_3$); 3.00(m, 2H, SCH$_2$); 2.00(m, 1H, SCH$_2$CH$_2$CH); 1.60(m, 2H, SCH$_2$CH$_2$); 1.45(t, 3H, OCH$_2$CH$_3$); 1.00(d, 6H, SCH$_2$CH$_2$CH(CH$_3$)$_2$)

Example 71: 9.30(d, 1H, CHS); 4.50(m, 2H, OCH$_2$); 4.60(d, 3H, NCH$_3$); 3.00(m, 2H, SCH$_2$); 1.70(m, 9H, OCH$_2$CH$_3$ and SCH$_2$CH$_2$CH$_2$CH$_2$CH$_3$); 1.00 (m, 3H, SCH$_2$CH$_2$CH$_2$CH$_2$CH$_3$)

Example 72: 9.30(d, 1H, CHS); 4.40(m, 2H, OCH$_2$); 3.50(d, 3H, NCH$_3$); 2.90(m, 2H, SCH$_2$); 2.00(m, 1H, SCH$_2$CH(CH$_3$)); 1.50(m, 8H, OCH$_2$CH$_3$ and SCH$_2$CH(CH$_3$)CH$_2$CH$_3$); 1.00(m, 3H, SCH$_2$CH(CH$_3$)CH$_2$CH$_3$)

Example 73: 9.35(d, 1H, CHS); 4.40(m, 2H, OCH$_2$); 3.55(m, 1H, SCH); 3.50 (d, 3H, NCH$_3$); 2.10(m, 2H, SCH(CH$_3$)CH$_2$); 1.60(m, 8H, OCH$_2$CH$_3$ and SCH(CH$_3$)CH$_2$CH$_2$CH$_3$); 1.10(m, 3H, SCH(CH$_3$)CH$_2$CH$_2$CH$_3$)

Example 74: 9.30(d, 1H, CHS); 6.00(m, 1H, SCH$_2$CH$_2$CH=CH$_2$); 5.30(m, 2H, SCH$_2$CH$_2$CH=CH$_2$); 4.50(m, 2H, OCH$_2$); 3.50(d, 3H, NCH$_3$); 3.10(m, 2H, SCH$_2$CH$_2$CH=CH$_2$); 2.65(m, 2H, SCH$_2$); 1.60(t, 3H, OCH$_2$CH$_3$).

Example 75: 9.30(d, 1H, CHS); 4.40(m, 2H, OCH$_2$); 3.60(m, 2H, SCH$_2$CH$_2$ OCH$_3$); 3.45(s, 3H, SCH$_2$CH$_2$OCH$_3$); 3.40(d, 3H, NCH$_3$); 3.00(m, 2H, SCH$_2$); 1.45(t, 3H, OCH$_2$CH$_3$)

Example 76: 9.30(d, 1H, CHS); 4.60(m, 2H, OCH$_2$); 3.60(d, 3H, NCH$_3$); 3.62(m, 1H, SCH); 1.78(m, 2H, SCH(CH$_3$)CH$_2$); 1.50(m, 3H, SCH(CH$_3$)); 1.00(m, 3H, SCH(CH$_3$)CH$_2$CH$_3$)

Example 77: 9.30(d, 1H, CHS); 4.40(m, 4H, OCH$_2$, NCH$_2$); 3.50(m, 1H, SCH); 1.80(m, 4H, OCH$_2$CH$_2$ and SCH(CH$_3$)CH$_2$); 1.50(m, 6H, NCH$_2$CH$_3$ and SCH(CH$_3$)CH$_2$CH$_3$); 1.10(m, 6H, OCH$_2$CH$_2$CH$_3$ and SCH(CH$_3$)CH$_2$CH$_3$)

TABLE III (cont.)-continued

Example 78: 9.30(d, 1H, CHS); 4.30(m, 2H, OCH₂); 3.50(d, 3H, NCH₃); 3.50(m, 1H, SCH); 1.80(m, 4H, SCH(CH₃)CH₂ and OCH₂CH₂); 1.50(t, 3H, SCH(CH₃)); 1.00(m, 6H, SCH(CH₃)CH₂CH₃ and OCH₂CH₂CH₃)

TABLE III (cont.)
Nuclear Magnetic Resonance Data (ppm, δ)

Example 79: 9.30(d, 1H, CHS); 4.90(d, 2H, NCH₂); 4.40(m, 2H, OCH₂); 3.80(s, 3H, NCH₂CO₂CH₃); 3.50(m, 1H, SCH); 1.80(m, 2H, SCH(CH₃)CH₂); 1.50(m, 6H, OCH₂CH₃ and SCH(CH₃)CH₂CH₃); 1.00(m, 3H, SCH(CH₃)CH₂CH₃)

Example 80: 9.28(d, 1H, CHS); 7.40(m, 5H, NCH₂C₆H₅); 5.65(m, 2H, NCH₂); 4.30(m, 2H, OCH₂); 3.50(m, 1H, SCH); 1.80(m, 2H, SCH(CH₃)CH₂); 1.50(m, 6H, OCH₂CH₃ and SCH(CH₃)CH₂); 1.10(m, 3H, SCH(CH₃)CH₂CH₃)

Example 81: 9.30(d, 1H, CHS); 7.40(m, 4H, NCH₂C₆H₄F); 5.50(m, 2H, NCH₂); 4.20(m, 2H, OCH₂); 3.40(m, 1H, SCH); 1.80(m, 2H, SCH(CH₃)CH₂); 1.50 (m, 6H, OCH₂CH₃ and SCH(CH₃)CH₂); 1.00(m, 3H, SCH(CH₃)CH₂CH₃)

Example 82: 9.30(d, 1H, CHS); 7.20(m, 4H, NCH₂C₆H₄OCH₃); 5.40 (m, 2H, NCH₂); 4.30 (m, 2H, OCH₂); 3.98(s, 3H, NCH₂C₆H₄OCH₃); 3.30(m, 1H, SCH); 1.80(m, 2H, SCH(CH₃)CH₂); 1.50(m, 6H, OCH₂CH₃ and SCH(CH₃)CH₂); 1.00 (m, 3H, SCH(CH₃)CH₂CH₃)

Example 83: 9.30(d, 1H, CHS); 7.60(m, 4H, NCH₂C₆H₄CF₃); 5.70(m, 2H, NCH); 4.40(m, 2H, OCH₂); 3.50(m, 1H, SCH); 1.80(m, 2H, SCH(CH₃)CH₂); 1.50(m, 6H, OCH₂CH₃ and SCH(CH₃)CH₂); 1.10(m, 3H, SCH(CH₃)CH₂CH₃)

Example 84: 9.25(d, 1H, CHS); 4.50(d, 2H, NCH₂); 4.40(m, 2H, OCH₂); 3.70(t, 2H, NCH₂CH₂CH₂Cl); 3.38(m, 1H, SCH); 2.40(m, 2H, NCH₂CH₂); 1.80(m, 2H, SCH(CH₃)CH₂); 1.50(m, 6H, OCH₂CH₃ and SCH(CH₃)); 1.00(m, 3H, SCH(CH₃)CH₂CH₃)

Example 85: 9.30(d, 1H, CHS); 7.50(m, 4H, NCH₂SC₆H₄Cl); 4.40(m, 2H, OCH₂); 3.60(m, 1H, SCH); 1.80(m, 2H, SCH(CH₃)CH₂); 1.50(m, 6H, OCH₂CH₃ and SCH(CH₃)); 1.10(m, 3H, SCH(CH₃)CH₂CH₃)

Example 86: 9.30(d, 1H, CHS); 5.60(m, 2H, NCH₂C(Br)=CH₂); 5.00(NCH₂); 4.50(m, 2H, OCH₂); 3.50(m, 1H, SCH); 1.80(m, 2H, SCH(CH₃)CH₂); 1.50 (m, 6H, OCH₂CH₃ and SCH(CH₃)CH₂); 1.10(m, 3H, SCH(CH₃)CH₂CH₃)

Example 87: 9.30(d, 1H, CHS); 7.40(m, 5H, NCH₂CH=CHC₆H₅); 6.60(m, 2H, CH₂CH=CH); 5.00(m, 2H, NCH₂); 4.30(m, 2H, OCH₂); 3.40(m, 1H, SCH); 1.80(m, 2H, SCH(CH₃)CH₂); 1.50(m, 6H, OCH₂CH₃ and SCH(CH₃)); 1.00(m, 3H, SCH(CH₃)CH₂CH₃)

Example 88: 9.30(d, 1H, CHS); 5.00(d, 2H, NCH₂); 4.60(m, 4H, OCH₂ and NCH₂CO₂CH₂CH₃); 3.60(m, 1H, SCH); 1.80(m, 2H, SCH(CH₃)CH₂); 1.50(m, 9H, OCH₂CH₃, NCH₂CO₂CH₂CH₃ and SCH(CH₃)); 1.20(m, 3H, SCH(CH₃)CH₂CH₃)

Example 89: 9.30(d, 1H, CHS); 4.38(m, 2H, OCH₂CH₂); 3.60(m, 2H, OCH₂ CH₂OCH₃); 3.39(d, 3H, NCH₃); 3.38(s, 3H, OCH₃); 3.38(m, 1H, SCH); 1.80 (m, 2H, SCH(CH₃)CH₂); 1.38(t, 3H, SCH(CH₃)); 1.00 (m, 3H, SCH(CH₃)CH₂CH₃)

Example 90: 9.35(d, 1H, CHS); 7.00, 6.00 and 5.20(m, 1H, HCF₂CH₂); 4.58 (m, 2H, OCH₂CF₂CF₂H); 3.50(m, 1H, SCH); 3.50(d, 3H, NCH₃); 1.80(m, 2H, SCH(CH₃)CH₂); 1.50(t, 3H, SCH(CH₃)); 1.00(m, 3H, SCH(CH₃)CH₂CH₃)

Example 91: 9.35(d, 1H, CHS); 4.60(m, 2H, OCH₂CF₃); 3.60(m, 1H, SCH); 3.60(m, 2H, NCH₂); 1.80(m, 2H, SCH(CH₃)CH₂); 1.60(m, 3H, SCH(CH₃)); 1.10(m, 3H, SCH(CH₃)CH₂CH₃)

Example 92: 9.30(d, 1H, CHS); 7.40(m, 5H, NCH₂SC₆H₅); 5.60(d, 2H, NCH₂); 4.40(m, 2H, OCH₂); 3.60(m, 1H, SCH); 1.80(m, 2H, SCH(CH₃)CH₂); 1.60(m, 3H, OCH₂CH₃, SCH(CH₃)); 1.10(m, 3H, SCH(CH₃)CH₂CH₃)

Example 93: 9.30(d, 1H, CHS); 5.98(m, 2H, NCH₂CH=CHCH₃); 4.90 (m, 2H OCH₂); 4.60(m, 2H, NCH₂); 3.50(m, 1H, SCH); 1.90(m, 2H, SCH(CH₃)CH₂); 1.80(m, 3H, NCH₂CH=CHCH₃); 1.60(m, 3H, OCH₂CH₃, SCH(CH₃)); 1.10(m, 3H, SCH(CH₃)CH₂CH₃)

Example 94: (d, 1H, CHS); 7.80(m, 4H, NCH₂C₆H₄); 5.40(m, 2H, NCH₂); 4.20(m, 2H, OCH₂); 3.30(m, 1H, SCH); 1.80(m, 2H, SCH(CH₃)CH₂); 1.50(m, 6H, OCH₂CH₃ and SCH(CH₃)); 1.00(m, 3H, SCH(CH₃)CH₂CH₃)

Example 121: 8.90(s, 1H, CHO); 4.40(d, 2H, NCH₂); 4.38(m, 2H, OCH₂); 3.85(s, 3H, NCH₂CO₂CH₃); 3.50(m, 1H, SCH); 1.80(m, 2H, SCH(CH₃)CH₂); 1.60(m, 9H, OCH₃, OCH₂CH₃, SCH(CH₃); 1.00(m, 3H, SCH(CH₃)CH₂CH₃)

Example 122: 8.85(s, 1H, CHO); 7.50(m, 5H, NCH₂CH₆H₅); 5.00(dd, 2H, NCH₂); 4.40(m, 2H, OCH₂); 3.50(m, 1H, SCH); 1.80(m, 2H, SCH(CH₃)CH₂); 1.60(m, 6H, OCH₃ and SCH(CH₃)); 1.00(m, 3H, SCH(CH₃)CH₂CH₃)

Example 123: 8.85(s, 1H, CHO); 7.40(m, 4H, NCH₂C₆H₄); 4.90(m, 2H, NCH₂); 4.40(m, 2H, OCH₂); 3.50(m, 1H, SCH); 1.80(m, 2H, SCH(CH₃)CH₂); 1.60(m, 6H, OCH₃ and SCH(CH₃)); 1.00 (m, 3H, SCH(CH₃)CH₂CH₃)

Example 124: 8.90(s, 1H, CHO); 7.30(m, 4H, NCH₂C₆H₄); 5.00(dd, 2H, NCH₂); 4.20(m, 2H, OCH₂); 3.90(s, 3H, OCH₃); 3.59(m, 1H, SCH); 1.80 (m, 2H, SCH(CH₃)CH₂); 1.55(m, 6H, OCH₃ and SCH(CH₃)); 1.00(m, 3H, SCH(CH₃)CH₂CH₃)

Example 125: 8.85(s, 1H, CHO); 7.80(m, 4H, NCH₂C₆H₄); 5.00(dd, 2H, NCH₂); 4.38(m, 2H, OCH₂); 3.50(m, 1H, SCH); 1.80(m, 2H, SCH(CH₃)CH₂); 1.59(m, 6H, OCH₃ and SCH(CH₃)); 1.10(m, 3H, SCH(CH₃)CH₂CH₃)

Example 126: 8.90(s, 1H, CHO); 4.40(m, 2H, OCH₂); 3.90(m, 2H, NCH₂); 3.80(m, 2H, NCH₂CH₂CH₂Cl); 3.409m, 1H, SCH); 2.38(m, 2H, NCH₂CH₂); 1.80(m, 2H, SCH(CH₃)CH₂); 1.55(m, 6H, OCH₂CH₃ and SCH(CH₃)); 1.10 (m, 3H, SCH(CH₃)CH₂CH₃)

Example 127: 8.90(s, 1H, CHO); 7.40(m, 4H, NCH₂SC₆H₄); 5.00(d, 2H, NCH₂); 4.20(m, 2H, OCH₂); 3.40(m, 1H, SCH); 1.75(m, 2H, SCH(CH₃)CH₂); 1.40(m, 6H, OCH₂CH₃ and SCH(CH₃)); 1.10(m, 3H, SCH(CH₃)CH₂CH₃)

Example 128: 8.90(s, 1H, CHO); 5.90(m, 2H, NCH₂C(BR)=CH₂); 4.60(m, 2H, NCH₂); 4.40(m, 2H, OCH₂); 3.50(m, 1H, SCH); 1.80(m, 2H, SCH(CH₃) CH₂); 1.55(m, 6H, OCH₂CH₃ and SCH(CH₃)); 1.10(m, 3H, SCH(CH₃)CH₂CH₃)

TABLE III (cont.)
Nuclear Magnetic Resonance Data (ppm, δ)

Example 129: 8.90(s, 1H, CHO); 7.40(s, 5H, NCH₂CH=CHC₆H₅); 6.80(d, 1H, NCH₂CH=CH); 6.40(m, 1H, NCH₂CH=CH); 4.60(m, 2H, NCH₂); 4.40(m, 2H, OCH₂); 3.50(m, 1H, SCH); 1.80(m, 2H, SCH(CH₃)CH₂); 1.55(m, 6H, OCH₂CH₃ and SCH(CH₃)); 1.10(m, 3H, SCH(CH₃)CH₂CH₃)

Example 130: 8.90(s, 1H, CHO); 4.40(d, 2H, NCH₂); 4.38(m, 4H, OCH₂ and NCH₂CO₂CH₂CH₃); 3.50(m, 1H, SCH); 1.80(m, 2H, SCH(CH₃)CH₂); 1.55 (m, 9H, OCH₂CH₃, NCH₂CO₂CH₂CH₃ and SCH(CH₃)); 1.10(m, 3H, SCH(CH₃) CH₂CH₃)

Example 131: 8.85(s, 1H, CHO); 8.00(m, 4H, NCH₂C₆H₄); 5.00(d, 2H, NCH₂); 4.20(m, 2H, OCH₂); 3.45(m, 1H, SCH); 1.80(m, 2H, SCH(CH₃)CH₂); 1.50(m, 6H, OCH₂CH₃ and SCH(CH₃)); 1.10(m, 3H, SCH(CH₃)CH₂CH₃)

Example 132: 8.90(s, 1H, CHO); 7.80(m, 4H, NCH₂C₆H₄); 5.00(dd, 2H, NCH₂); 3.40(m, 2H, OCH₂); 3.50(m, 1H, SCH); 1.80(m, 2H, SCH(CH₃) CH₂); 1.50(m, 6H, OCH₂CH₃ and SCH(CH₃)); 1.10(m, 3H, SCH(CH₃)CH₂CH₃)

TABLE III (cont.)-continued

Example 133: 8.90(s, 1H, CHO); 8.00(m, 5H, NCH$_2$COC$_6$H$_5$); 5.20(d, 2H, NCH$_2$); 3.40(m, 2H, OCH$_2$); 3.50(m, 1H, SCH); 1.80(m, 2H, SCH(CH$_3$)CH$_2$); 1.55(m, 6H, OCHCH$_2$CH$_3$ and SCH(CH$_3$)); 1.10(m, 3H, SCH(CH$_3$)CH$_2$CH$_3$)

Example 134: 8.90(s, 1H, CHO); 7.50(m, 4H, NCH$_2$C$_6$H$_4$); 5.00(d, 2H, NCH$_2$); 4.40(m, 2H, OCH$_2$); 3.50(m, 1H, SCH), 1.80(m, 2H, SCH(CH$_3$)CH$_2$); 1.50(m, 6H, OCH$_2$CH$_3$ and SCH(CH$_3$)); 1.10(m, 3H, SCH(CH$_3$)CH$_2$CH$_3$)

Example 135: 8.90(s, 1H, CHO); 7.30(m, 4H, NCH$_2$OC$_6$H$_4$); 5.70(d, 2H, NCH$_2$); 4.30(m, 2H, OCH$_2$); 3.50(m, 1H, SCH); 1.80(m, 2H, SCH(CH$_3$)CH$_2$); 1.55(m, 6H, OCH$_2$CH$_3$ and SCH(CH$_3$)); 1.10(m, 3H, SCH(CH$_3$)CH$_2$CH$_3$)

Example 136: 8.90(s, 1H, CHO); 7.78(m, 7H, NCH$_2$C$_{10}$H$_7$); 5.10(dd, 2H, NCH$_2$); 4.00(m, 2H, OCH$_2$); 3.40(m, 1H, SCH); 1.80(m, 2H, SCH(CH$_3$)CH$_2$); 1.60(m, 6H, OCH$_2$CH$_3$ and SCH(CH$_3$)); 1.00(m, 3H, SCH(CH$_3$)CH$_2$CH$_3$)

Example 137: 8.90(s, 1H, CHO); 5.80(m, 2H, NCH$_2$CH=CHCH$_3$); 4.40(m, 4H, OCH$_2$ and NCH$_2$); 3.40(m, 1H, SCH); 1.90(m, 5H, SCH(CH$_3$) and NCH$_2$CH=CHCH$_3$); 1.50(m, 6H, OCH$_2$CH$_3$ and SCH(CH$_3$)); 1.10(m, 3H, SCH(CH$_3$)CH$_2$CH$_3$)

Example 138: 8.90(s, 1H, CHO); 7.48(m, 3H, NCH$_2$C$_6$H$_3$); 5.30(dd, 2H, NCH$_2$); 4.30(m, 2H, OCH$_2$); 3.50(m, 1H, SCH); 1.80(m, 2H, SCH(CH$_3$)CH$_2$); 1.50(m, 6H, OCH$_2$CH$_3$ and SCH(CH$_3$)); 1.10(m, 3H, SCH(CH$_3$)CH$_2$CH$_3$)

Example 139: 8.85(s, 1H, CHO); 5.10(d, 2H, NCH$_2$); 4.40(m, 2H, OCH$_2$); 3.50(m, 1H, SCH); 1.80(m, 2H, SCH(CH$_3$)CH$_2$); 1.50(m, 6H, OCH$_2$CH$_3$ and SCH(CH$_3$)); 1.10(m, 3H, SCH(CH$_3$)CH$_2$CH$_3$)

Example 140: 8.90(s, 1H, CHO); 4.40(m, 2H, OCH$_2$); 3.50(m, 2H, NCH$_2$); 2.75(m, 2H, SCH$_2$); 1.50(m, 9H, NCH$_2$CH$_2$CH$_2$CH$_3$, OCH$_2$CH$_3$ and SCH$_2$CH$_2$CH$_3$); 1.00(m, 6H, SCH$_2$CH$_2$CH$_3$ and NCH$_2$CH$_2$CH$_2$CH$_3$)

Example 141: 8.90(s, 1H, CHO); 7.39(m, 5H, NCH$_2$C$_6$H$_5$); 4.80(m, 2H, NCH$_2$); 4.00(m, 2H, OCH$_2$); 2.70(m, 2H, SCH$_2$); 1.70(m, 2H, SCH$_2$CH$_2$); 1.20(m, 6H, SCH$_2$CH$_2$CH$_3$ and OCH$_2$CH$_3$)

Example 142: 8.90(s, 1H, CHO); 4.40(m, 6H, NCH$_2$, OCH$_2$, NCH$_2$CO$_2$CH$_2$); 3.00(m, 2H, SCH$_2$); 1.70(m, 2H, SCH$_2$CH$_2$); 1.20(m, 9H, SCH$_2$CH$_2$CH$_3$, OCH$_2$CH$_3$ and NCH$_2$CO$_2$CH$_2$CH$_3$)

Example 143: 8.85(s, 1H. CHO); 4.60(m, 4H, OCH$_2$ and NCH$_2$); 3.90(m, 2H. NCH$_2$CH$_2$CH$_2$Cl); 3.10(m, 2H, SCH$_2$); 2.20(m, 2H, NCH$_2$CH$_2$); 1.80(m, 2H, SCH$_2$CH$_2$); 1.50(m, 3H, OCH$_2$CH$_3$); 1.00(m, 3H, SCH$_2$CH$_2$CH$_2$)

Example 144: 8.90(s, 1H, CHO); 7.80(m, 9H, NCH$_2$C$_6$H$_4$OCH$_2$C$_6$H$_5$); 5.30(s, 2H, NCH$_2$C$_6$H$_4$OCH$_2$); 5.00(m, 2H, NCH$_2$); 4.40(m, 2H, OCH$_2$); 3.40(m, 1H, SCH); 1.80(m, 2H, SCH(CH$_3$)CH$_2$); 1.50(m, 6H, OCH$_2$CH$_3$ and SCH(CH$_3$)); 1.00(m, 3H, SCH(CH$_3$)CH$_2$CH$_3$)

Example 146: 8.90(s, 1H, CHO); 5.10(m, 2H, NCH$_2$C(CH$_3$)=CH$_2$); 4.30 (m, 4H, OCH$_2$ and NCH$_2$); 3.50(m, 1H, SCH); 1.80(s, 3H, NCH$_2$C(CH$_3$)=CH$_2$); 1.45(m, 6H, OCH$_2$CH$_3$ and SCH(CH$_3$)); 1.00(m, 3H, SCH(CH$_3$)CH$_2$CH$_3$)

Example 148: 8.90(s, 1H, CHO); 7.50(s, 5H, NCH$_2$C$_6$H$_5$); 5.00(dd, 2H, NCH$_2$); 4.20(m, 2H, OCH$_2$); 3.40(m, 1H, SCH); 1.80(m, 2H, SCH(CH$_3$) CH$_2$); 1.50(m, 6H, OCH$_2$CH$_3$ and SCH(CH$_3$)); 1.00(m, 3H, SCH(CH$_3$)CH$_2$CH$_3$)

Example 152: 8.90(s, 1H, CHO); 7.38(m, 4H, NCH$_2$C$_6$H$_4$); 4.78(m, 2H, NCH$_2$); 4.20(m, 2H, OCH$_2$); 3.40(m, 1H, SCH); 1.80(m, 2H, SCH(CH$_3$)CH$_2$); 1.50(m, 6H, OCH$_2$CH$_3$ and SCH(CH$_3$)); 1.00(m, 3H, SCH(CH$_3$)CH$_2$CH$_3$)

Example 159: 8.85(s, 1H, CHO); 8.00(m, 4H, NCH$_2$C$_6$H$_4$); 4.90(dd, 2H, NCH$_2$); 4.30(m, 2H, OCH$_2$); 3.40(m, 1H, SCH); 1.80(m, 2H, SCH(CH$_3$)CH$_2$); 1.50(m, 6H, OCH$_2$CH$_3$ and SCH(CH$_3$)); 1.10(m, 3H, SCH(CH$_3$)CH$_2$CH$_3$)

Example 165: 8.90(s, 1H, CHO); 5.00(m, 2H, NCH$_2$); 4.38(m, 2H, OCH$_2$); 3.50(m, 1H, SCH); 1.80(m, 2H, SCH(CH$_3$)CH$_2$); 1.50(m, 6H, OCH$_2$CH$_3$ and SCH(CH$_3$)); 1.10(m, 3H, SCH(CH$_3$)CH$_2$CH$_3$)

Example 176: 8.90(s, 1H, CHO); 8.00(m, 3H, NCH$_2$C$_6$H$_3$); 4.90(dd, 2H, NCH$_2$); 4.40(m, 2H, OCH$_2$); 3.40(m, 1H, SCH); 2.70(s, 3H, NCH$_2$C$_6$H$_3$CH$_3$); 1.80(m, 2H, SCH(CH$_3$)CH$_2$); 1.50(m, 6H, OCH$_2$CH$_3$ and SCH(CH$_3$)); 1.10 (m, 3H, SCH(CH$_3$)CH$_2$CH$_3$)

Example 180: 8.85(s, 1H, CHO); 7.70(m, 4H, NCH$_2$C$_6$H$_4$); 4.90(dd, 2H, NCH$_2$); 4.39(m, 2H, OCH$_2$); 3.50(m, 1H, SCH); 1.80(m, 2H, SCH(CH$_3$)CH$_2$); 1.50(m, 6H, OCH$_2$CH$_3$ and SCH(CH$_3$)); 1.10(m, 3H, SCH(CH$_3$)CH$_2$CH$_3$)

Table IV which follows sets forth the biological data obtained as described above for the exemplary compounds described in Table I.

| Code Symbol | Common Name | Latin Name |
|---|---|---|
| TSM | Two-spotted spider mite | *Tetranychus urticae* |
| GPA | Green peach aphid | *Myzus persicae* |
| CRW | Southern corn rootworm | *Diabrotica undecimpunctata howardi* |
| NEMA | Southern root-knot nematode | *Meloidogyne incognita* |

A test solution containing 600 ppm of test compound in a solvent (acetone:methanol, 1:1) and then adding water to give an acetone:methanol:water system of 5:5:90. A test solution containing 150 ppm of test compound is prepared by diluting 1 part of 600 ppm test solution with three parts of water. A 1:1 mixture of alkylarlpolyetheralcohol (commercially available under the trademark TRITON ® X-155) and a modified phthalic glycerol alkyl resin (commercially available under the trademark TRITON ® B-1956) is utilized at the equivalent of one ounce per 100 gallons of test solution as a surfactant.

For the mite test, infested bean (*Phaseolus limeanus*) leaf section (~1×1 inches) containing about 50 mites are placed in a Petri dish lid on a moistened piece of cotton. The leaves are then sprayed with the 600 ppm test solution using a rotating turntable. They are held for 24 hours and then the percent kill is determined.

For the aphid test, infected broccoli (*Brassica oleracea*) leaf section (~1×1 inches) containing about 30 adult and mymphal aphids are placed in a Petri dish lid on a moistened piece of cotton. The leaves are then sprayed with the 600 ppm test solution using a rotating turntable. They are held for 24 hours and then the percent kill is determined.

For the rootworm larvae test, ten milliliters of the 150 ppm test solution are added to 200 milliliter of soil in a 16 oz. jar to give a concentration by volume of about 8 ppm. The jar is shaken to insure thorough mixing, immediately uncapped, and allowed to ai for 2 hours. Two presoaked kernels of Golden Cross Bantam corn (*Zea map*) are placed in the bottom of a 1 oz. plastic cap and covered with about 30 grams of treated soil. The soil surface is inoculated with approximately 120 southern corn rootworm eggs and the plastic cup closed iwth a tight-fitting cap. The test cup is held for 10 days at 27° C. and then the percent kill relative to the untreated check is determined.

For the nematode test, soil is homogenously inoculated with nematode eggs at the rate of about 5000 eggs per 200 milliliters of soil extracted from a macerated blend of tomato roots heavily knotted with the root knot nematode. Ten milliliters of the 150 ppm test solution are added to 200 milliliters of the inoculated soil in a 16 oz. jar to give a concentration by volume of about 8 ppm. The jar is shaken to insure thorough mixing, immediatley uncapped, and allowed to air for 24 hours. The soil is then placed into a 3-inch plastic pot after which time 3 cucumber (*Cucumis sativus*) seeds are planted. About 23 days thereafter, the cucumber plants are removed from the soil and root system examined for the presence of knots. A total of 25 knots or less is considered as a measure of control. Excellent control is characterized by 0–2 knots.

TABLE IV

Pesticidal Activity % Control[a]

| Example | Soil Application (150 ppm) CRW | NEMA | Foliar Application (600 ppm) TSM | GPA |
|---|---|---|---|---|
| 1 | 100 | +++++ | 100 | 98 |
| 2 | 100 | — | 100 | 50 |
| 3 | 100 | — | 0 | 0 |
| 4 | 62 | — | 0 | 0 |
| 5 | 65 | +++++ | 100 | 100 |
| 6 | 100 | +++++ | 100 | 100 |
| 7 | 100 | +++++ | 100 | 100 |
| 8 | 27 | +++++ | 0 | 0 |
| 9 | 100 | +++ | 100 | 95 |
| 10 | 100 | — | 100 | NA |
| 11 | 100 | — | 100 | 100 |
| 12 | 98 | +++++ | 81 | 0 |
| 13 | 100 | — | 100 | 100 |
| 14 | 100 | ++++ | 100 | 100 |
| 15 | 0 | — | 84 | 0 |
| 16 | 100 | — | 100 | 100 |
| 17 | | | | |
| 18 | 100 | ++++ | 100 | 73 |
| 19 | | | | |
| 20 | | | | |
| 21 | 22 | — | 0 | 0 |
| 22 | 100 | +++++ | 100 | 100 |
| 23 | 100 | +++++ | 100 | 0 |
| 24 | 100 | +++++ | 100 | 0 |
| 25 | 100 | +++++ | 100 | 100 |
| 26 | 100 | +++ | 100 | 100 |
| 27 | 100 | +++++ | 100 | 100 |
| 28 | 100 | +++++ | 100 | 100 |
| 29 | 100 | +++++ | 100 | 100 |
| 30 | 100 | +++++ | 100 | 100 |
| 31 | 100 | ++++ | 100 | 100 |
| 32 | 100 | +++++ | 100 | 100 |
| 33 | 100 | +++++ | 100 | 100 |
| 34 | 100 | +++ | 100 | 100 |
| 35 | 100 | +++++ | 100 | 100 |
| 36 | 100 | NA | 100 | 100 |
| 37 | 100 | +++++ | 100 | 100 |
| 38 | 100 | +++++ | 100 | 100 |
| 39 | 100 | +++++ | 100 | 100 |
| 40 | 100 | — | 100 | 95 |
| 41 | 100 | +++++ | 100 | 100 |
| 42 | 100 | +++++ | 100 | 100 |
| 43 | | | | |
| 44 | 100 | +++++ | 100 | 100 |
| 45 | 100 | — | 89 | 100 |
| 46 | 100 | +++++ | 100 | 100 |
| 47 | 100 | +++++ | 100 | 100 |
| 48 | 100 | +++++ | 100 | 100 |
| 49 | 100 | +++ | 100 | 100 |
| 50 | 100 | — | 100 | 76 |
| 51 | 97 | NA | NA | NA |
| 52 | 100 | +++ | 100 | 0 |
| 53 | 100 | ++++ | 100 | 0 |
| 54 | 96 | — | 100 | 29 |
| 55 | 100 | — | 100 | NA |
| 56 | 100 | +++++ | 100 | NA |
| 57 | 100 | — | 100 | 100 |
| 58 | 100 | +++ | 100 | 100 |
| 59 | 100 | — | 100 | 40 |
| 60 | 100 | — | 0 | 100 |
| 61 | 100 | ++ | 59 | 100 |
| 62 | 100 | — | 97 | 0 |
| 63 | 100 | NA | 100 | 100 |
| 64 | 94 | — | 100 | 100 |
| 65 | 100 | +++++ | 100 | 83 |
| 66 | 100 | — | 100 | 100 |
| 67 | 100 | ++++ | 100 | 73 |
| 68 | 100 | +++ | 100 | 100 |
| 69 | 100 | — | 100 | 11 |
| 70 | 100 | — | 100 | 0 |
| 71 | 83 | — | 100 | 93 |
| 72 | 100 | — | 100 | 100 |
| 73 | 100 | — | 100 | 100 |
| 74 | 70 | — | 100 | 100 |
| 75 | 100 | — | 100 | 100 |
| 76 | 100 | ++++ | 100 | 100 |
| 77 | 100 | — | 0 | 100 |
| 78 | 100 | — | 51 | 100 |
| 79 | 99 | NA | 100 | 100 |
| 80 | 100 | ++ | 100 | 100 |
| 81 | 100 | — | 100 | 100 |
| 82 | 100 | — | 100 | 100 |
| 83 | 100 | ++ | 100 | 100 |
| 84 | 100 | — | 100 | 100 |
| 85 | 100 | — | 100 | 100 |
| 86 | 100 | — | 100 | 100 |
| 87 | 100 | +++ | 100 | 100 |
| 88 | 100 | +++ | 100 | 100 |
| 89 | 82 | +++++ | 100 | 100 |
| 90 | 100 | +++++ | 100 | 100 |
| 91 | 100 | +++++ | 33 | 0 |
| 92 | 100 | — | 100 | 100 |
| 93 | 100 | — | 100 | 100 |
| 94 | 99 | — | 100 | 100 |
| 95 | 100 | +++++ | 100 | 100 |
| 96 | 100 | — | 100 | 100 |
| 97 | 100 | — | 100 | 100 |
| 98 | 100 | +++++ | 100 | 100 |
| 99 | 89 | +++++ | 100 | 91 |
| 100 | 100 | ++++ | 100 | 100 |
| 101 | 100 | — | 100 | 100 |
| 102 | 100 | +++++ | 100 | 100 |
| 103 | 100 | — | 100 | 100 |
| 104 | 100 | ++++ | 100 | 100 |
| 105 | 100 | ++++ | 100 | 100 |
| 106 | 100 | +++ | 100 | 100 |
| 107 | 100 | +++++ | 100 | 100 |
| 108 | 100 | +++++ | 100 | 100 |
| 109 | 100 | +++++ | 100 | 100 |
| 110 | 97 | — | 100 | 100 |
| 111 | 99 | ++++ | 100 | 100 |
| 112 | 100 | +++ | 100 | 100 |
| 113 | 100 | +++++ | 100 | 100 |
| 114 | 100 | +++++ | 100 | 100 |
| 115 | 100 | +++++ | 100 | 100 |
| 116 | 98 | +++++ | 100 | 100 |
| 117 | 100 | +++ | 100 | 100 |
| 118 | 100 | — | 100 | 100 |
| 119 | 95 | +++ | 100 | 100 |
| 120 | 90 | — | 100 | 100 |
| 121 | 98 | +++++ | 100 | 100 |
| 122 | 100 | ++++ | 100 | 100 |
| 123 | 100 | ++ | 100 | 100 |
| 124 | 100 | — | 100 | 100 |
| 125 | 100 | — | 100 | 100 |
| 126 | 100 | — | 100 | 100 |
| 127 | 100 | — | 100 | 100 |
| 128 | 100 | +++ | 100 | NA |
| 129 | 100 | — | 100 | 100 |
| 130 | 100 | — | 100 | 100 |
| 131 | 100 | — | 100 | 100 |
| 132 | 100 | — | 100 | 100 |
| 133 | 100 | — | 100 | 100 |
| 134 | 100 | — | 100 | 100 |

TABLE IV-continued

| | Pesticidal Activity % Control[a] | | | |
|---|---|---|---|---|
| | Soil Application (150 ppm) | | Foliar Application (600 ppm) | |
| Example | CRW | NEMA | TSM | GPA |
| 135 | 100 | — | 100 | 100 |
| 136 | 100 | — | 100 | 100 |
| 137 | 100 | — | 100 | 95 |
| 138 | 100 | — | 100 | 100 |
| 139 | 100 | — | 100 | 100 |
| 140 | 100 | ++ | 100 | 100 |
| 141 | 100 | — | 100 | 100 |
| 142 | 100 | ++++ | 100 | 100 |
| 143 | 100 | ++ | 100 | 100 |
| 144 | 98 | — | 100 | 100 |
| 145 | 100 | — | 100 | 100 |
| 146 | 100 | ++ | 100 | 100 |
| 147 | 100 | | 100 | 100 |
| 148 | 100 | | 100 | 100 |
| 149 | 100 | +++ | 100 | 100 |
| 150 | 100 | +++++ | 100 | 100 |
| 151 | 100 | +++++ | 100 | 100 |
| 152 | 100 | +++++ | 100 | 100 |
| 153 | 100 | +++++ | 100 | 100 |
| 154 | 100 | +++++ | 100 | 100 |
| 155 | 100 | ++++ | 100 | 100 |
| 156 | 100 | +++++ | 100 | 100 |
| 157 | 100 | +++++ | 100 | 100 |
| 158 | 100 | +++++ | 100 | 100 |
| 159 | 99 | ++++ | 100 | 100 |
| 160 | 100 | +++++ | 100 | 100 |
| 161 | 98 | +++++ | 100 | 100 |
| 162 | 98 | +++++ | 100 | 100 |
| 163 | 100 | +++++ | 100 | 100 |
| 164 | 100 | +++++ | 100 | 100 |
| 165 | 100 | +++++ | 100 | 100 |
| 166 | 100 | +++ | 100 | 100 |
| 167 | 100 | +++++ | 100 | 100 |
| 168 | 100 | +++++ | 100 | 100 |
| 169 | 100 | +++++ | 100 | 100 |
| 170 | 100 | | 100 | 100 |
| 171 | 94 | +++++ | 100 | 100 |
| 172 | 98 | +++++ | 100 | 100 |
| 173 | 100 | +++++ | 100 | 100 |
| 174 | 100 | +++++ | 100 | 100 |
| 175 | 100 | +++++ | 100 | 100 |
| 176 | 98 | +++++ | 100 | 100 |
| 177 | 100 | +++++ | 100 | 100 |
| 178 | 100 | +++ | 100 | 100 |
| 179 | 100 | +++++ | NT | NT |
| 180 | 0 | +++++ | 100 | 100 |

CRW = Southern Corn Rootworm
NEMA = Southern Root Knot Nematode
TSM = Two Spotted Spider Mite
GPA = Green Peach Aphid
NA = Not Available

| Rank | Knots |
|---|---|
| +++++ | 0-2 |
| ++++ | 3-6 |
| +++ | 7-9 |
| ++ | 18-25 |
| — | 25+ |

[a]CRW, TSM, & GPA - Test results expressed as % control.
NEMA - Test results expressed as rankings for degree of knotting.

What is claimed is:

1. A compound having the formula

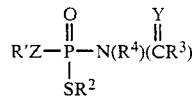

wherein:
$R^1$ is unsubstituted or substituted $(C_1-C_4)$alkyl wherein the substituent can be from one to four of the same or different bromo, chloro or fluoro groups;
$R^2$ is unsubstituted straight or branched chain $(C_2-C_5)$alkyl;
$R^3$ is hydrogen;
$R^4$ is unsubstituted or substituted $(C_3-C_6)$alkenyl wherein the substituent can be from one to three of the same or different phenyl, alkyl, carbo$(C_1-C_4)$alkoxy, bromo, chloro or fluoro groups; $(C_3-C_6)$alkynyl; unsubstituted or substituted phenyl wherein the substituent can be from one to five of the same or different halo or from one to three of the same or different alkyl, haloalkyl containing one to three of the same or different halo, alkoxy, alkylthio, cyano, nitro, amino, or mono- or dialkylamino, wherein the alkyl moiety is straight or branched chain and contains from one to three carbon atoms; or unsubstituted or substituted phenyl$(C_1-C_3)$alkyl wherein the substituent on the phenyl ring can be from one to five of the same or different halo or from one to three of the same or different alkyl, haloalkyl containing one to three of the same or different halo, alkoxy, alkylthio, benzyloxy, methylenedioxy, cyano, nitro, amino, or mono— or dialkylamino groups, wherein the alkyl moiety is straight or branched chain and contains from one to three carbon atoms; and Y and Z are O.

2. A method of controlling arthropods which comprises applying directly to the arthropods or to the locus to be freed or protected from attack by arthropods an arthropodicidally effective amount of an active compound according to claim 1.

3. A compound according to claim 1 wherein:
$R^1$ is unsubstituted $(C_1-C_4)$alkyl;
$R^2$ is unsubstituted branched chain $(C_2-C_5)$alkyl;
$R^3$ is hydrogen; and $R^4$ is $(C_3-C_6)$alkenyl; $(C_3-C_6)$alkynyl; or unsubstituted or substituted phenyl$(C_1-C_3)$alkyl wherein the substituent on the phenyl ring can be from one to three of the same or different alkyl, haloalkyl, halo, alkoxy, alkylthio, cyano, nitro, amino, or mono— and dialkylamino groups, wherein the alkyl moiety is straight or branched chain and contains from one to three carbon atoms and Y and Z are O.

4. A compound according to claim 3 wherein:
$R^1$ is unsubstituted straight or branched chain $(C_2-C_4)$alkyl;
$R^2$ is unsubstituted branched chain $(C_2-C_5)$alkyl;
$R^3$ is hydrogen; and
$R^4$ is unsubstituted or substituted benzyl wherein the substituent on the phenyl ring can be from one to three of the same or different $(C_1-C_3)$alkyl, fluoro, chloro, bromo, methoxy, trifluoromethyl, nitro or cyano.

5. A compound according to claim 4 wherein:
$R^1$ is ethyl;
$R^2$ is unsubstituted branched chain $(C_2-C_5)$alkyl;
$R^3$ is hydrogen; and
$R^4$ is substituted benzyl wherein the substituent on the phenyl ring can be from one to two of the same or different $(C_1-C_3)$alkyl, fluoro, chloro, bromo, methoxy, trifluoromethyl, nitro or cyano.

6. A compound according to claim 5 wherein:
$R^1$ is ethyl;
$R^2$ is 1-methylpropyl
$R^3$ is hydrogen; and
$R^4$ is 4-fluorobenzyl.

7. A compound according to claim 5 wherein:

$R^1$ is ethyl;
$R^2$ is 1-methylpropyl;
$R^3$ is hydrogen; and
$R^4$ is 4-nitrobenzyl.

8. A compound according to claim 5 wherein:
$R^1$ is ethyl;
$R^2$ is 1-methylpropyl;
$R^3$ is hydrogen; and
$R^4$ is 4-cyanobenzyl.

9. A compound according to claim 5 wherein
$R^1$ is ethyl;
$R^2$ is 1-methylpropyl;
$R^3$ is hydrogen; and
$R^4$ is 4-trifluoromethylbenzyl.

10. A compound according to claim 5 wherein
$R^1$ is ethyl;
$R^2$ is 1-methylpropyl;
$R^3$ is hydrogen; and
$R^4$ is 3-trifluoromethylbenzyl.

11. An arthropodicide composition which comprises an arthropodicidally effective amount of a compound according to claim 1.

12. An arthropodicide composition which comprises an arthropodicidally effective amount of a compound according to claim 5.

13. A method of controlling arthropods which comprises applying directly to the arthropods or to the locus to be freed or protected from attack by arthropods an arthropodicidally effective amount of an active compound according to claim 5.

14. A method of controlling soil arthropods which comprises applying on or in soil so as to permit direct contact with arthropods an arthropodicidally effective amount of an active compound according to claim 1.

15. A method of controlling soil arthropods which comprises applying on or in soil so as to permit direct contact with arthropods an arthropodicidally effective amount of an active compound according to claim 5.

16. A compound having the formula

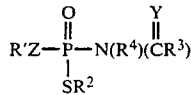

wherein:
$R^1$ is unsubstituted or substituted $(C_1-C_4)$alkyl wherein the substituent can be from one to four of the same or different bromo, chloro or fluoro groups; unsubstituted or substituted phenyl wherein the substituent can be from one to three of the same or different alkyl, haloalkyl, halo, alkoxy, alkylthio, cyano, nitro, amino, or mono- or dialkylamino, wherein the alkyl moiety is straight or branched chain and contains from one to three carbon atoms; or unsubstituted or substituted phenyl$(C_1-C_3)$alkyl wherein the substituent on the phenyl ring can be from one to three of the same or different alkyl, haloalkyl containing one to three of the same or different halo, alkoxy, alkylthio, cyano, nitro, amino, or mono- and dialkylamino groups, wherein the alkyl moiety is straight or branched chain and contains from one to three carbon atoms;
$R^2$ is unsubstituted straight or branched chain $(C_2-C_5)$alkyl or substituted $(C_2-C_5)$alkyl wherein the substituent can be from one to three of the same or different alkyl, halo, alkoxy, alkylthio, cyano, nitro, amino, or mono— or dialkylamino, wherein the alkyl moiety is straight or branched chain and contains from one to three carbon atoms; $(C_3-C_6)$alkenyl; or $(C_3-C_6)$alkynyl;
$R^3$ is hydrogen;
$R^4$ is unsubstituted or substituted $(C_1-C_7)$alkyl wherein the substituent can be one to three of the same or different carbo$(C_1-C_4)$alkoxy, halo, alkoxy, alkylthio, cyano, nitro, unsubstituted or substituted phenoxy or phenylthio wherein the substituent can be from one to three of the same or different alkyl, alkoxy, halo, cyano, nitro, or alkylthio, or amino or mono— or dialkylamino, wherein the alkyl moiety is straight or branched chain and contains from one to three carbon atoms; unsubstituted or substituted $(C_3-C_6)$alkenyl wherein the substituent can be from one to three of the same or different phenyl, alkyl, carbo$(C_1-C_4)$alkoxy, bromo, chloro or fluoro groups; $(C_3-C_6)$alkynyl; unsubstituted or substituted phenyl wherein the substituent can be from one to five of the same or different halo or from one to three of the same or different alkyl, haloalkyl containing one to three of the same or different halo, alkoxy, alkylthio, cyano, nitro, amino, or mono— or dialkylamino, wherein the alkyl moiety is straight or branched chain and contains from one to three carbon atoms; or unsubstituted or substituted phenyl$(C_1-C_3)$alkyl wherein the substituent on the phenyl ring can be from one to five of the same or different halo or from one to three of the same or different alkyl, haloalkyl containing one to three of the same or different halo, alkoxy, alkylthio, benzyloxy, methylenedioxy, cyano, nitro, amino, or mono— or dialkylamino groups, wherein the alkyl moiety is straight or branched chain and contains from one to three carbon atoms;
Y is S; and
Z is O.

17. A method of controlling arthropods which comprises applying directly to the arthropods or to the locus to be freed or protected from attack by arthropods an arthropodicidally effective amount of an active compound according to claim 16.

18. A compound according to claim 16 wherein:
$R^1$ is unsubstituted or substituted $(C_1-C_4)$alkyl wherein the substituent can be from one to three of the same or different bromo, chloro or fluoro groups; unsubstituted or substituted phenyl wherein the substituent can be from one to three of the same or different alkyl, haloalkyl, halo, alkoxy, alkylthio, cyano, nitro, amino, or mono— or dialkylamino, wherein the alkyl moiety is straight or branched chain and contains from one to three carbon atoms; or unsubstituted or substituted phenyl$(C_1-C_3)$alkyl wherein the substituent on the phenyl ring can be from one to three of the same or different alkyl, haloalkyl, halo, alkoxy, alkylthio, cyano, nitro, amino, or mono— or dialkylamino groups, wherein the alkyl moiety is straight or branched chain and contains from one to three cabon atoms;
$R^2$ is unsubstituted straight or branched chain $(C_2-C_5)$alkyl or substituted $(C_2-C_5)$alkyl wherein the substituent can be from one to three of the same or different alkyl, halo, alkoxy, alkylthio, cyano, nitro, amino, or mono— or dialkylamino, wherein the alkyl moiety is straight or branched chain and contains from one to three carbon atoms; or (C$_3$–C$_6$)alkenyl;

R$^3$ is hydrogen; and

R$^4$ is unsubstituted or substituted (C$_1$–C$_7$)alkyl wherein the substituent can be one to three of the same or different carbo(C$_1$–C$_4$)alkoxy, halo, alkoxy, alkylthio; (C$_3$–C$_6$)alkenyl; (C$_3$–C$_6$)alkynyl; or unsubstituted or substituted phenyl(C$_1$–C$_3$)alkyl wherein the substituent on the phenyl ring can be from one to three of the same or different alkyl, haloalkyl, halo, alkoxy, alkylthio, cyano, nitro, amino, or mono— or dialkylamino groups, wherein the alkyl moiety is straight or branched chain and contains from one to three carbon atoms.

19. A compound according to claim 18 wherein

R$^1$ is unsubstituted straight or branched chain (C$_2$–C$_4$)alkyl, 2-fluoroethyl, 2,2,2-trifluoroethyl, phenyl or benzyl;

R$^2$ is unsubstituted straight or branched chain (C$_2$–C$_5$)alkyl;

R$^3$ is hydrogen; and

R$^4$ is unsubstituted or substituted (C$_1$–C$_4$)alkyl wherein the substituent can be alkylthio where the alkyl moiety is straight or branched chain and contains from one to three carbon atoms; propenyl; or unsubstituted or substituted benzyl wherein the substituent on the phenyl ring can be from one to three of the same or different (C$_1$–C$_3$)alkyl, fluoro, chloro, bromo, methoxy, trifluoromethyl, nitro or cyano.

20. A compound according to claim 19 wherein:

R$^1$ is ethyl;

R$^2$ is unsubstituted straight or branched chain (C$_2$–C$_5$)alkyl;

R$^3$ is hydrogen; and

R$^4$ is methyl, ethyl, propyl, butyl, methylthiomethyl, propenyl, or benzyl.

21. A compound according to claim 20 wherein:

R$^1$ is ethyl;

R$^2$ is 1-ethylpropyl;

R$^3$ is hydrogen; and

R$^4$ is ethyl.

22. A compound according to claim 20 wherein:

R$^1$ is ethyl;

R$^2$ is 1-methylpropyl;

R$^3$ is hydrogen; and

R$^4$ is methyl.

23. A compound according to claim 20 wherein:

R$^1$ is ethyl;

R$^2$ is n-propyl;

R$^3$ is hydrogen; and

R$^4$ is methyl.

24. A compound according to claim 20 wherein:

R$^1$ is ethyl;

R$^2$ is 1-methylpropyl;

R$^3$ is hydrogen; and

R$^4$ is 2-propenyl.

25. A compound according to claim 20 wherein:

R$^1$ is ethyl;

R$^2$ is 1-methylpropyl;

R$^3$ is hydrogen; and

R$^4$ is methyl.

26. A compound according to claim 20 wherein:

R$^1$ is ethyl;

R$^2$ is 1-methylpropyl;

R$^3$ is hydrogen; and

R$^4$ is methylthiomethyl.

27. A compound according to claim 20 wherein:

R$^1$ is ethyl;

R$^2$ is 1-methylpropyl;

R$^3$ is hydrogen; and

R$^4$ is benzyl.

28. A compound according to claim 20 wherein:

R$^1$ is ethyl;

R$^2$ is 1-methylpropyl;

R$^3$ is hydrogen; and

R$^4$ is n-propyl.

29. A compound according to claim 20 wherein:

R$^1$ is ethyl;

R$^2$ is 1-methylpropyl;

R$^3$ is hydrogen; and

R$^4$ is n-butyl.

30. A compound according to claim 20 wherein:

R$^1$ is ethyl;

R$^2$ is 1-methylpropyl;

R$^3$ is hydrogen; and

R$^4$ is ethyl.

31. A compound according to claim 20 wherein:

R$^1$ is ethyl;

R$^2$ is n-propyl;

R$^3$ is hydrogen; and

R$^4$ is n-butyl.

32. A compound according to claim 20 wherein:

R$^1$ is ethyl;

R$^2$ is ethyl;

R$^3$ is hydrogen; and

R$^4$ is methyl.

33. A compound according to claim 20 wherein:

R$^1$ is ethyl;

R$^2$ is i-propyl;

R$^3$ is hydrogen; and

R$^4$ is methyl.

34. An arthropodicide composition which comprises an arthropodicidally effective amount of a compound according to claim 16.

35. An arthropodicide composition which comprises an arthropodicidally effective amount of a compound according to claim 20.

36. A method of controlling arthropods which comprises applying directly to the arthropods or to the locus to be freed or protected from attack by arthropods an arthropodicidally effective amount of an active compound according to claim 20.

37. A method of controlling soil arthropods which comprises applying on or in soil so as to permit direct contact with arthropods an arthropodicidally effective amount of an active compound according to claim 16.

38. A method of controlling soil arthropods which comprises applying on or in soil so as to permit direct contact with arthropods an arthropodicidally effective amount of an active compound according to claim 20.

* * * * *